(12) United States Patent
Lyng et al.

(10) Patent No.: US 9,809,859 B2
(45) Date of Patent: Nov. 7, 2017

(54) BIOMARKERS FOR SUBTYPES OF CERVICAL CANCER

(71) Applicant: Oslo universitetssykehus HF, Oslo (NO)

(72) Inventors: Heidi Lyng, Lommedalen (NO); Malin Lando, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 0 days.

(21) Appl. No.: 14/664,346

(22) Filed: Mar. 20, 2015

(65) Prior Publication Data
US 2015/0197818 A1 Jul. 16, 2015

Related U.S. Application Data

(62) Division of application No. 13/045,671, filed on Mar. 11, 2011, now abandoned.

(60) Provisional application No. 61/312,875, filed on Mar. 11, 2010.

(51) Int. Cl.
*C12Q 1/68* (2006.01)
*G01N 33/574* (2006.01)

(52) U.S. Cl.
CPC ..... *C12Q 1/6886* (2013.01); *G01N 33/57411* (2013.01); *C12Q 2600/106* (2013.01); *C12Q 2600/118* (2013.01); *C12Q 2600/136* (2013.01); *C12Q 2600/158* (2013.01); *C12Q 2600/16* (2013.01); *G01N 2333/4703* (2013.01); *G01N 2333/4704* (2013.01); *G01N 2333/4706* (2013.01); *G01N 2333/91131* (2013.01)

(58) Field of Classification Search
None
See application file for complete search history.

(56) References Cited

U.S. PATENT DOCUMENTS

| | | | | |
|---|---|---|---|---|
| 2004/0029124 A1 * | 2/2004 | Zohlnhofer | ........ | C12N 15/1096 435/6.16 |
| 2005/0233363 A1 * | 10/2005 | Harding | .............. | B01L 3/50851 435/6.16 |

FOREIGN PATENT DOCUMENTS

WO   WO 0060126 A2 * 10/2000 ........... C12Q 1/6837

OTHER PUBLICATIONS

Bachtiary et al., Gene Expression Profiling in Cervical Cancer: An Exploration of Intratumor Heterogeneity; Clin Cancer Res, vol. 12, No. 19, pp. 5632-5640, 2006.*

Lando et al., 2009, "Integrated genomic and transcriptional profiling of cervical cancers reveals candidate biomarkers of chemoradioresistant disease." Abstract for the Fourth International Conference on Translational Research and Pre-Clinical Strategies in Radiation Oncology (ICTR), Mar. 11-13, 2009. (Abstract Only).
Lyng et al., 2009, 11th International Wolfsberg Meeting on Molecular Radiation Biology/Oncology Jun. 27-29, 2009. Published in Proceeding of the 11th International Wolfsberg Meeting on Molecular Radiation Biology/Oncology (2009) p. 68. (Abstract Only).
Lyng et al., 2004, "Intratumor chromosomal heterogeneity in advanced carcinomas of the uterine cervix." Int J Cancer 111:358-366.
Lyng et al., 2008, "GeneCount: genome-genomic calculation of absolute tumor DNA copy numbers from array comparative genomic hybridization data." Genome Biol 9: R86.
Heselmeyer et al., 1997, "Advanced-stage cervical carcinomas are defined by a recurrent pattern of chromosomal aberrations revealing high genetic instability and a consistent gain of chromosome arm 3q." Genes Chromosomes Cancer 19: 233-240.
Kirchhoff et al., 1999, "Comparative genomic hybridization reveals a recurrent pattern of chromosomal aberrations in severe dysplasia/carcinoma in situ of the cervix and in advanced-stage cervical carcinoma." Genes Chromosomes Cancer 24: 144-150.
Imoth et al., 2002, "Expression of cIAP1, a target for 11q22 amplification, correlates with resistance of cervical cancers to radiotherapy." Cancer Res 62: 4860-4866.
Narayan et al., 2007, "Gene dosage alterations revealed by cDNA microarray analysis in cervical cancer: identification of candidate amplified and overexpressed genes." Genes Chromosomes Cancer 46: 373-384.
Scotto et al., 2008, "Identification of copy number gain and overexpressed genes on chromosome arm 20q by an integrative genomic approach in cervical cancer: potential role in progression." Genes Chromosomes Cancer 47: 755-765.
Scotto et al., 2008, "Integrative genomics analysis of chromosome 5p gain in cervical cancer reveals target over-expressed genes, including Drosha." Mol Cancer 7:58.
Wilting et al., 2008, "Integrated genomic and transcriptional profiling identifies chromosomal loci with altered gene expression in cervical cancer." Genes Chromosomes Cancer 47: 890-905.
Wilting et al., 2009, "Chromosomal signatures of a subset of high-grade premalignant cervical lesions closely resemble invasive carcinomas." Cancer Res 69: 647-655.
Alazawi et al., "Genomic imbalances in 70 snap-frozen cervical squamous intraepithelial lesions: associations with lesion grade, state of the HPV 16 E2 gene and clinical outcome", British Journal of Cancer, vol. 91, pp. 2063-2070, 2004.

* cited by examiner

*Primary Examiner* — Addison D Ault
(74) *Attorney, Agent, or Firm* — Casimir Jones S.C.

(57) ABSTRACT

The present invention relates to biomarkers for chemoradioresistant subtypes of cervical cancer. In particular the present invention relates to a method for predicting a predisposition to a chemoradioresistant cervical cancer in a subject, a method for diagnosing a chemoradioresistant cervical cancer in a subject, a method for predicting the likelihood of recurrence of cervical cancer in a cervical cancer patient under treatment, and a method for predicting the prognosis for a patient with a chemoradioresistant cervical cancer.

9 Claims, 19 Drawing Sheets

BIOMARKERS FOR SUBTYPES OF CERVICAL CANCER

CROSS REFERENCE TO RELATED APPLICATIONS

This application is a divisional of pending U.S. patent application Ser. No. 13/045,671, filed Mar. 11, 2011, which claims the benefit of U.S. Provisional Appl. 61/312,875, filed Mar. 11, 2010, the entire contents of which are incorporated herein by reference.

FIELD OF THE INVENTION

The present invention relates to biomarkers for subtypes of cervical cancer. In particular the present invention relates to a method for predicting a predisposition to a chemoradioresistant cervical cancer in a subject, a method for diagnosing a chemoradioresistant cervical cancer in a subject, a method for predicting the likelihood of recurrence of cervical cancer in a cervical cancer patient under treatment, and a method for predicting the prognosis for a patient with a chemoradioresistant cervical cancer.

BACKGROUND OF THE INVENTION

Cervical cancer is one of the most common malignancies affecting women worldwide and a major cause of cancer death for women globally. Radiotherapy combined with cisplatin is the treatment of choice at the locally advanced stages. Improved therapy is needed, since more than 30% of the patients show progressive disease within 5 years after diagnosis and treatment related side effects to organs within the pelvis are frequent. Tumor stage, size, and lymph node involvement are the most powerful markers of aggressive disease, but do not fully account for the observed variability in outcome and are not biologically founded.

A better handling of the disease may be provided by the discovery of efficient biomarkers for therapeutic planning and intervention, but requires more insight into the mechanisms underlying cervical carcinogenesis and treatment relapse.

During carcinogenesis, genetic and epigenetic alterations drive the evolution of tumor towards increased malignancy and treatment resistance. The changes enable tumor cells to overcome microenvironmental constraints, sustain proliferation, and invade adjacent tissues and distinct organs. Gene dosage alterations like gains and losses regulate the expression of genes and are motive forces for this evolution.

Tumor cells bearing an increasing number of gains and losses successively emerge and are selected for based on the growth advantage caused by the genetic changes. Discovery and functional assessment of gene dosage alterations involved in carcinogenesis are therefore essential for understanding the biology of the disease.

At the locally advanced stages of cervical cancer, numerous gene dosage alterations and severe aneuploidy are frequently seen. Moreover, pronounced intratumor heterogeneity in the gains and losses exists within the tumors, reflecting a high genetic instability.

The consequences of these alterations for the tumor phenotype are difficult to predict, since large chromosomal regions involving multiple genes are generally affected and some aberrations may be random events without biological significance. Genome wide screening of DNA copy numbers in a decent number of patients enables identification of recurrent gene dosage alterations; i.e., alterations characteristic of the disease, and alterations associated with the clinical outcome, which are likely to be important in carcinogenesis and treatment resistance.

Combining the data with expression profiles of the same tumors reveals the genes that are regulated primarily by the genetic events. The potential of this integrative strategy was recently demonstrated in a study on 15 early stage cervical cancers, where genes affected by aberrations on 1q, 3q, 11q, and 20q were reported.

Genetic events promoting tumor evolution and treatment resistance have, however, not been explored on a genome wide scale, and their biological meaning has not been addressed.

SUMMARY OF THE INVENTION

Thus, in some embodiments, the present invention provides improved biomarkers and methods for predicting a predisposition, diagnosing, predicting the likelihood of recurrence, predicting the prognosis for patient with a subtype of cervical cancer.

In particular, the present invention provides the above mentioned biomarkers and methods for predicting a predisposition, diagnosing, predicting the likelihood of recurrence predicting the prognosis for patient with a subtype of cervical cancer which is resistant to chemotherapy and/or radiotherapy.

Accordingly, in some embodiments, the present invention provides methods for predicting a predisposition to a subtype of cervical cancer in a subject, comprising
  providing a sample obtained from said subject,
  determining the gene dosage of at least one chromosomal region selected from the group consisting of 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q01.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3,
wherein alteration in gene dosage in said at least one chromosomal region indicates a predisposition to a subtype of cervical cancer.

In some embodiments, the present invention provides methods for diagnosing a subtype of cervical cancer in a subject, comprising
  providing a sample obtained from said subject,
  determining the gene dosage of at least one chromosomal region selected from the group consisting of 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q01.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3,
wherein the alteration in gene dosage indicates that the subject has a subtype of cervical cancer.

In some embodiments, the present invention provides methods for predicting the likelihood of recurrence of cervical cancer in a cervical cancer patient previously subjected to or under a course of therapeutic treatment of said cancer, comprising providing a sample obtained from said subject,
determining the gene dosage of at least one chromosomal region selected from the group consisting of 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q01.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3,
wherein the alteration in gene dosage indicates the likelihood of recurrence of cervical cancer.

In some embodiments, the present invention provides methods for predicting the prognosis for patient with a subtype of cervical cancer, comprising
providing a sample obtained from said subject,
determining the gene dosage of at least one chromosomal region selected from the group consisting of 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q01.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3,
wherein the alteration in gene dosage indicate poor survival of said patient.

In some embodiments, the present invention provides methods for predicting a predisposition to a subtype of cervical cancer in a subject, comprising
providing a sample obtained from said subject,
determining the expression levels of at least one gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK11IP, FARSB, ACSL3, HRB, SP100, EIF4E2, COPSE, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15,
wherein the alteration in the expression level of said at least one gene relative to a standard expression level of said at least one gene indicate a predisposition to said a subtype of cervical cancer.

In some embodiments, the present invention provides methods for diagnosing a subtype of cervical cancer in a subject, comprising
providing a sample obtained from said subject,
determining the expression levels of at least one gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK11IP, FARSB, ACSL3, HRB, SP100, EIF4E2, COPSE, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15,
wherein the alteration in the expression level of said at least one gene relative to a standard expression level of said at least one gene indicates a that the subject has a subtype of cervical cancer.

In some embodiments, the present invention provides methods for predicting the likelihood of recurrence of cervical cancer in a cervical cancer patient previously subjected to or under a course of therapeutic treatment of said cancer, comprising
providing a sample obtained from said subject,
determining the expression levels of at least one gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK11IP, FARSB, ACSL3, HRB, SP100, EIF4E2, COPS8, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15,
wherein the alteration in the expression level of said at least one gene relative to a standard expression level of said at least one gene indicates the likelihood of recurrence of cervical cancer.

In some embodiments, the present invention provides methods for predicting the prognosis for patient with a subtype of cervical cancer, comprising
providing a sample obtained from said subject,
determining the expression levels of at least one gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK11IP, FARSB, ACSL3, HRB, SP100, EIF4E2, COPS8, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15,
wherein the alteration in the expression level of said at least one gene relative to a standard expression level of said at least one gene indicates poor survival of said patient.

In some embodiments, the present invention provides methods for predicting efficacy of a treatment of a subtype of cervical cancer in a subject, comprising
providing a sample obtained from said subject,
determining the gene dosage of at least one chromosomal region selected from the group consisting of 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q01.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3,
wherein alteration in gene dosage in said at least one chromosomal region indicates a poor efficacy of said treatment of a subtype of cervical cancer.

In some embodiments, the present invention provides methods for predicting efficacy of a treatment of a subtype of cervical cancer in a subject, comprising
providing a sample obtained from said subject,
determining the expression levels of at least one gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK11IP, FARSB, ACSL3, HRB, SP100, EIF4E2, COPSE, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15, wherein the alteration in the expression level of said at least one gene relative to a standard expression level of said at least one gene indicates a poor efficacy of said treatment of a subtype of cervical cancer.

Further aspects of the invention concern any of the above methods where the subtype of cervical cancer is a subtype of cervical cancer resistant to chemotherapy and/or radiotherapy (radiation therapy/radiation oncology).

DEFINITIONS

Figure 1:
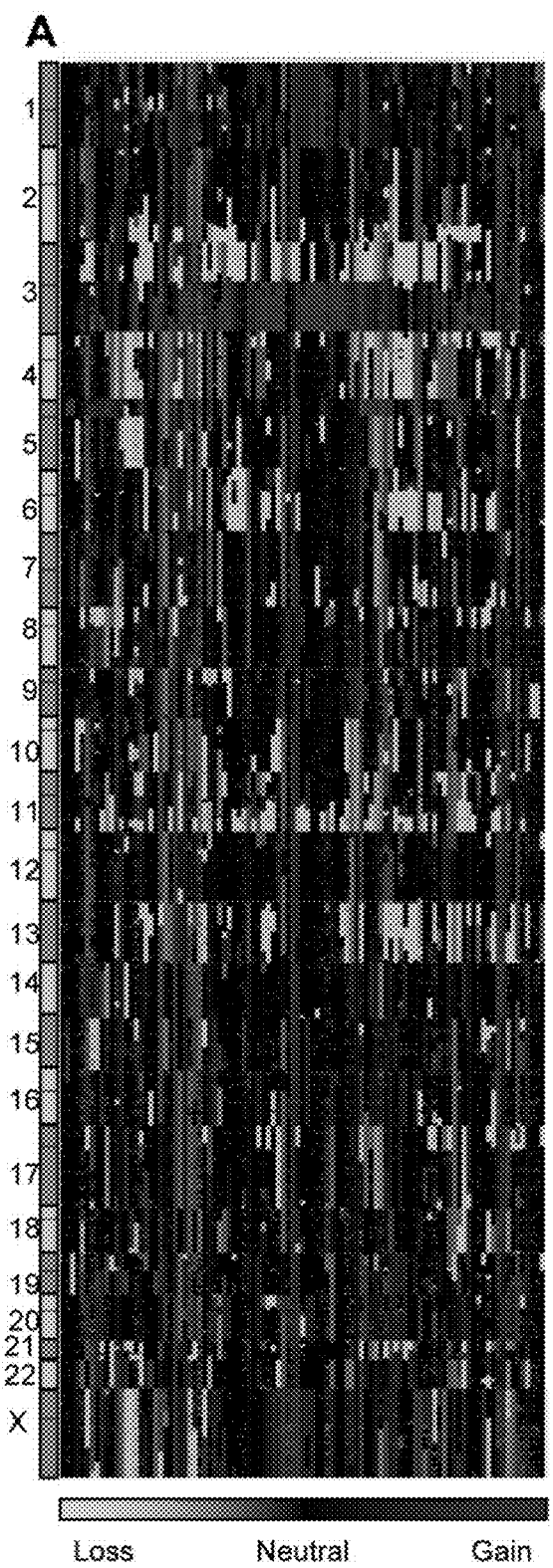
FIG. 1. Gene dosage alterations of locally advanced cervical cancers. (A) Absolute gene dosage profile of 97 patients. Patients are shown in columns and gene dosages are ordered by DNA location in rows. The color scale ranges from bright gray (loss) through black (neutral) to dark gray (gain). Grey indicates missing values. (B) Frequency of patients with gains (dark gray) and losses (bright gray) along chromosome 1 to X for the patients in (A). Gene dosage alterations above 1.1 and below 0.9 were classified as gains and losses, respectively. (C) Score of recurrent gains (dark gray) and losses (bright gray) along chromosome 1 to X for the patients in (A). Peak regions, defined in Table 2, are shown in darker colors. (D) Intratumor heterogeneity in gene dosage alterations along chromosome 1 to X for the patients in (A). The heterogeneity index is shown for gains (above the zero line) and losses (below the zero line) separately, and was calculated as the number of heterogeneous cases relative to the total number of cases with alteration at each DNA location. The peak regions shown in (C) are marked in black (recurrent gains) and dark gray (recurrent losses). The predictive losses are indicated in bright gray.
Figure 1:
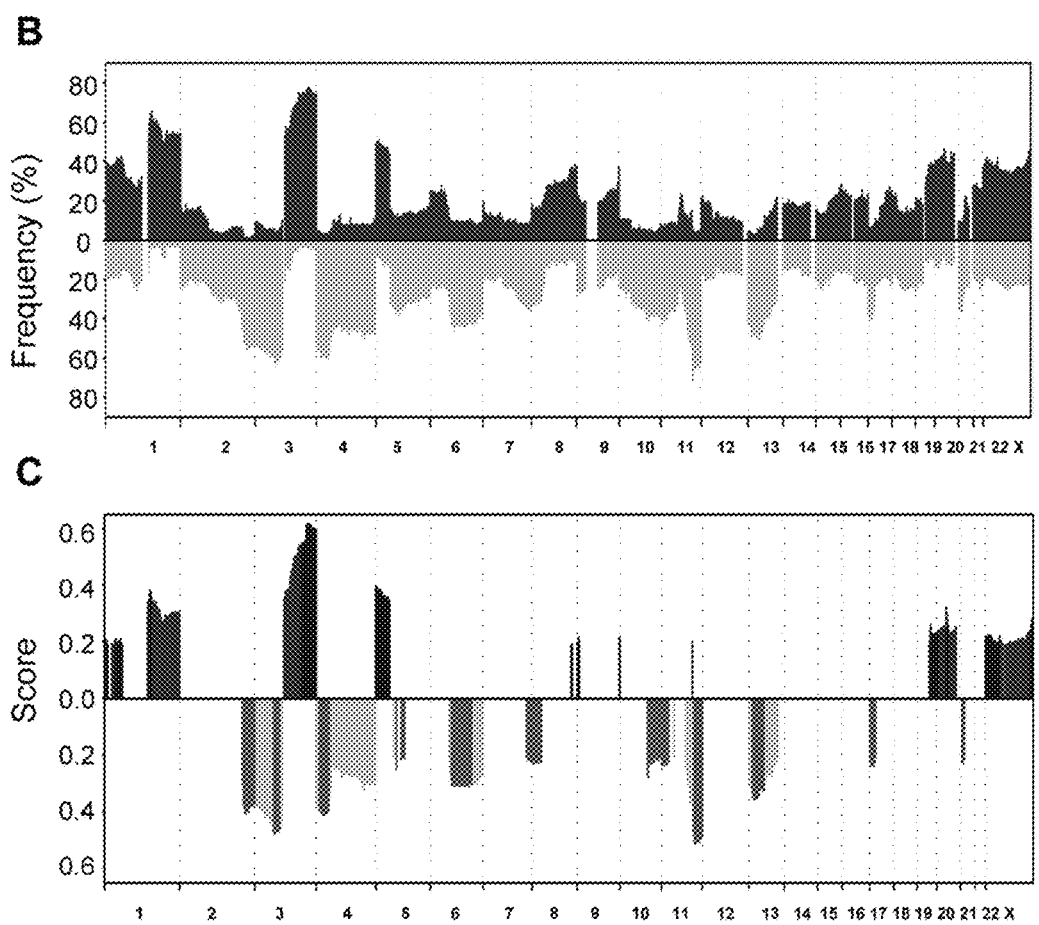
Figure 1:
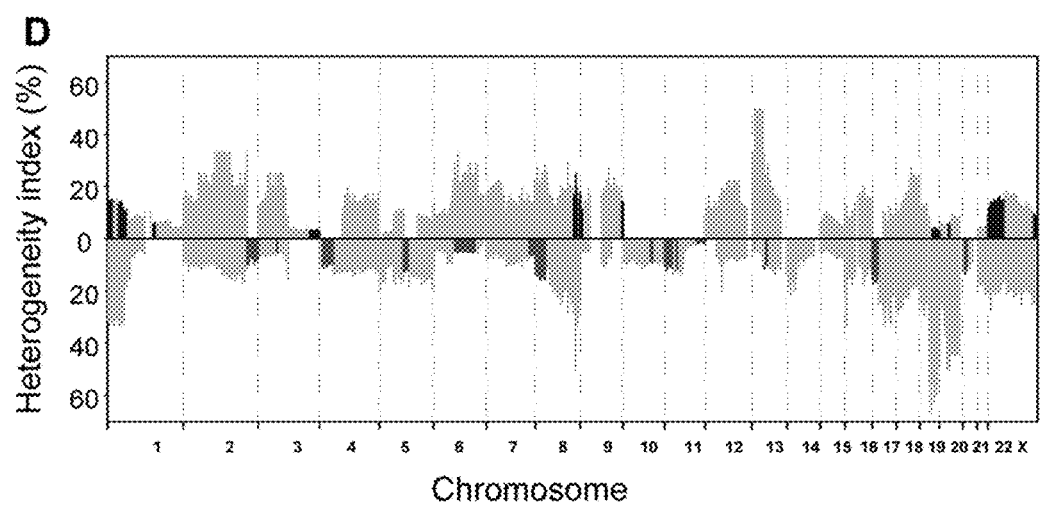

Prior to discussing the present invention in further details, the following terms and conventions will first be defined:

As used herein, the term "sample" relates to any liquid or solid sample collected from an individual to be analyzed. In one embodiment, the sample is liquefied at the time of assaying. In another embodiment, the sample is suspension of single cells disintegrated from a tissue biopsy such as a tumor biopsy. In some embodiments, the sample is a tissue sample, for example, a tissue section mounted on a slide. In some embodiments, the sample comprises genomic DNA, mRNA or rRNA. In another embodiment of the present invention, a minimum of handling steps of the sample is necessary before measuring the expression of a RNA/cDNA. In the present context, the subject "handling steps" relates to any kind of pre-treatment of the liquid sample before or after it has been applied to the assay, kit or method. Pre-treatment procedures includes separation, filtration, dilution, distillation, concentration, inactivation of interfering compounds, centrifugation, heating, fixation, addition of reagents, or chemical treatment. In accordance with the present invention, the sample to be analyzed is collected from any kind of mammal, including a human being, a pet animal, and a zoo animal. In yet another embodiment of the present invention, the sample is derived from any source such as body fluids. Preferably, this source is selected from the group consisting of milk, semen, blood, serum, plasma, saliva, faeces, urine, sweat, ocular lens fluid, cerebral spinal fluid, cerebrospinal fluid, ascites fluid, mucous fluid, synovial fluid, peritoneal fluid, vaginal discharge, vaginal secretion, cervical discharge, cervical or vaginal swab material or pleural, amniotic fluid and other secreted fluids, substances, cultured cells, and tissue biopsies. One embodiment of the present invention relates to a method according to the present invention, wherein said body sample or biological sample is selected from the group consisting of blood, vaginal washings, cervical washings, cultured cells, tissue biopsies such as cervical biopsies, and follicular fluid. Another embodiment of the present invention relates to a method according to the present invention, wherein said biological sample is selected from the group consisting of blood, plasma and serum. The sample taken may be dried for transport and future analysis. Thus the method of the present invention includes the analysis of both liquid and dried samples.

As used herein, the term "chromosome region" refers to a portion of a chromosome. Several chromosome regions have been defined by convenience in order refer to the location of genes, for example the distinction between chromosome region p and chromosome region q. In diploid organisms, homologous chromosomes get attached to each other by the centromere. The centromere divides each chromosome into two regions: the smaller one, which is the p region, and the bigger one, the q region. At either end of a chromosome is a telomere, and the areas of the p and q regions close to the telomeres are the subtelomeres, or subtelomeric regions. The areas closer to the centromere are the pericentronomic regions. Finally, the interstitial regions are the parts of the p and q regions that are close to neither the centromere nor the telomeres, but are roughly in the middle of p or q. The chromosomal region may be further defined by reference to the conventional banding pattern of the chromosome. For example, 3p11.2 refers to chromosome 3, p arm, with the numbers that follow the letter representing the position on the arm: band 1, section 1, sub-band 2. The bands are visible under a microscope when the chromosome is suitably stained. Each of the bands is numbered, beginning with 1 for the band nearest the centromere. Sub-bands and sub-sub-bands are visible at higher resolution. As a further example, 3p11.2-p14.1, refers to the region on the p arm of chromosome 3 from band 1, section 1, sub-band 2 to band 1, section 4, sub-band 1.

The term "dosage" as used herein refers to the number of copies of a chromosomal region, or portion thereof, or a gene present in a cell or nucleus. Thus, the "chromosomal region dosage" is the number of copies of a particular chromosomal region, or portion thereof, in a cell or nucleus. Likewise, the "gene dosage" is the number of copies of a particular gene in a cell or nucleus.

The genes described herein are identified by the following gene accession numbers:

| Gene Symbol | UGRepAcc |
|---|---|
| AAMP | NM_001087 |
| ABCF3 | NM_018358 |
| ACSL3 | NM_004457 |
| AGTRAP | NM_001040194 |
| AHCY | NM_000687 |
| ALG3 | NM_001006941 |
| ALG5 | NM_001142364 |
| AMD1 | NM_001033059 |
| ANKZF1 | NM_001042410 |
| ANXA9 | NM_003568 |
| AP2S1 | NM_004069 |
| APLP2 | NM_001142276 |
| ARHGEF12 | NM_015313 |
| ARNT | NM_001668 |
| ARSD | NM_001669 |
| ATF5 | NM_012068 |
| ATP5J | NM_001003696 |
| BCAP31 | NM_001139441 |
| BDH1 | NM_004051 |
| BIN3 | NM_018688 |
| BIRC2 | NM_001166 |
| BIRC3 | NM_001165 |
| BNIP3L | NM_004331 |
| C11orf57 | NM_001082969 |
| C11orf60 | NM_001168618 |
| C1orf149 | NM_022756 |
| C1orf77 | NM_015607 |
| C6orf203 | NM_001142468 |
| CAPN12 | NM_144691 |
| CCDC25 | NM_018246 |
| CCDC50 | NM_174908 |
| CCNC | NM_001013399 |
| CCT5 | NM_012073 |

| Gene Symbol | UGRepAcc |
|---|---|
| CD99 | NM_001122898 |
| CGN | NM_020770 |
| CHEK1 | NM_001114121 |
| CLPTM1L | NM_030782 |
| COG6 | NM_001145079 |
| COPB1 | NM_001144061 |
| COPS3 | NM_003653 |
| COPS8 | NM_006710 |
| COX7C | NM_001867 |
| CXorf15 | NM_001168683 |
| CYB5D1 | NM_144607 |
| CYC1 | NM_001916 |
| DAP | NM_004394 |
| DCTN6 | NM_006571 |
| DDX3X | NM_001356 |
| DENND4B | NM_014856 |
| DGKG | NM_001080744 |
| DLG1 | NM_001098424 |
| DSE | NM_001080976 |
| DVL3 | NM_004423 |
| EBNA1BP2 | NM_001159936 |
| EBP | NM_006579 |
| ECHDC1 | NM_001002030 |
| EFNA1 | NM_004428 |
| EIF2S2 | NM_003908 |
| EIF2S3 | NM_001415 |
| EIF4A2 | NM_001967 |
| EIF4E2 | NM_004846 |
| EIF4G1 | NM_004953 |
| ENSA | NM_004436 |
| EPHX2 | NM_001979 |
| FAM3A | NM_001171132 |
| FAM48A | NM_001014286 |
| FAM83H | NM_198488 |
| FARSB | NM_005687 |
| FASTKD3 | NM_024091 |
| FDPS | NM_001135821 |
| FOXO3 | NM_001455 |
| FXR1 | NM_001013438 |
| FYTTD1 | NM_001011537 |
| GBE1 | NM_000158 |
| GLRX | NM_001118890 |
| GOLPH3L | NM_018178 |
| GTF2F2 | NM_004128 |
| GTF2H1 | NM_001142307 |
| H2AFX | NM_002105 |
| HDAC2 | NM_001527 |
| HDAC4 | NM_006037 |
| HIP2/UBE2K | NM_005339 |
| HMGN3 | NM_004242 |
| HRB | NM_001135187 |
| HUWE1 | NM_031407 |
| IDH3G | NM_004135 |
| ILF2 | NM_004515 |
| IRAK1 | NM_001025242 |
| JARID1C | NM_004187 |
| KDELR1 | NM_006801 |
| KIAA0020 | NM_014878 |
| KIAA1704 | NM_018559 |
| KIF3B | NM_004798 |
| KRTCAP2 | NM_173852 |
| LAGE3 | NM_006014 |
| LASS2 | NM_022075 |
| LMBRD1 | NM_018368 |
| LSMD1 | NM_032356 |
| MAP3K7 | NM_003188 |
| MAPRE1 | NM_012325 |
| MED10 | NM_032286 |
| MED4 | NM_014166 |
| MPDU1 | NM_004870 |
| MREG | NM_018000 |
| MRPS12 | NM_021107 |
| MRPS2 | NM_016034 |
| MTCP1 | NM_001018025 |
| MTERFD2 | NM_182501 |
| MUC1 | NM_001018016 |
| MYO6 | NM_004999 |
| NCBP2 | NM_001042540 |
| NDUFB11 | BQ278575 |
| NDUFS1 | NM_005006 |
| NKG7 | NM_005601 |
| NSDHL | NM_001129765 |
| NT5DC1 | NM_152729 |
| NUP62 | NM_012346 |
| NUS1 | NM_138459 |
| PAK2 | NM_002577 |
| PARL | NM_001037639 |
| PDCD10 | NM_007217 |
| PDHA1 | NM_000284 |
| PDIA4 | NM_004911 |
| PDS5A | NM_001100399 |
| PHC3 | NM_024947 |
| PHKA2 | NM_000292 |
| PIR | NM_001018109 |
| PLP2 | NM_002668 |
| PNPLA4 | NM_001142389 |
| POFUT1 | NM_015352 |
| POGZ | NM_015100 |
| POU2F3 | NM_014352 |
| PPP1R2 | NM_006241 |
| PPP1R7 | NM_002712 |
| PPP2CB | NM_001009552 |
| PPP2R1B | NM_002716 |
| PRDM15 | AF426260 |
| PRDX4 | NM_006406 |
| PRPS2 | NM_001039091 |
| PSMA1 | NM_001143937 |
| PSMD8 | NM_002812 |
| RCL1 | NM_005772 |
| REXO2 | NM_015523 |
| RFC4 | NM_002916 |
| RLF | NM_012421 |
| RNASEH2B | NM_001142279 |
| RPS16 | NM_001020 |
| RPS6KA3 | NM_004586 |
| RYBP | NM_012234 |
| SC5DL | NM_001024956 |
| SF3B4 | NM_005850 |
| SFRS10 | AB209208 |
| SLC25A6 | NM_001636 |
| SLC35E2 | NM_182838 |
| SLC39A1 | NM_014437 |
| SMARCAL1 | NM_014140 |
| SMC1A | NM_006306 |
| SMN2 | NM_017411 |
| SNTA1 | NM_003098 |
| SNX19 | NM_014758 |
| SNX27 | NM_030918 |
| SP100 | NM_001080391 |
| SPAG16 | NM_001025436 |
| SPAG7 | NM_004890 |
| SPINT2 | NM_001166103 |
| STK11IP | NM_052902 |
| SYNCRIP | NM_001159673 |
| TACSTD2 | NM_002353 |
| TAZ | NM_000116 |
| TIMM8B | NM_012459 |
| TRAPPC4 | NM_016146 |
| TSG101 | NM_006292 |
| TSTA3 | NM_003313 |
| TTC37 | NM_014639 |
| UBA1 | NM_003334 |
| UBE2Q1 | NM_017582 |
| UBE4B | NM_001105562 |
| UBL4A | NM_014235 |
| USP9X | NM_001039590 |
| WDR1 | NM_005112 |
| WNT10A | BC052234 |
| XPO7 | NM_001100161 |
| YAP1 | NM_001130145 |
| YRDC | NM_024640 |
| ZBTB44 | NM_014155 |
| ZFAND2B | NM_138802 |
| ZNF202 | NM_003455 |

| Gene Symbol | UGRepAcc |
| --- | --- |
| ZNF639 | NM_016331 |
| ZNF787 | NM_001002836 |

The term "cervical cancer" as used herein refers to a malignant neoplasm of the cervix uteri or cervical area. A typical treatment consists of surgery (including local excision) in early stages and chemotherapy and radiotherapy in advanced stages of the disease. Following chemotherapy and radiotherapy, the cervical cancer may relapse as a subtype of cervical cancer resistant to the at least one of the presently available chemotherapies or radiotherapies. Accordingly, in one embodiment of the present invention the cervical cancer is a subtype of cervical cancer, which is resistant to at least one chemotherapeutic and/or one radiotherapy. In a further embodiment, the subtype cervical cancer is resistant to cisplatin treatment and/or cisplatin treatment in combination with radiotherapy. In yet a further embodiment the subtype of cervical cancer is resistant to all presently available chemotherapeutics and/or presently available radiotherapies.

DETAILED DESCRIPTION OF THE INVENTION

The present invention provides methods, kits and systems that utilize biomarkers subtypes of cervical cancer. In some preferred embodiments, the present invention provides methods for predicting a predisposition to a cervical cancer in a subject, methods for diagnosing a cervical cancer in a subject, methods for predicting the likelihood of recurrence of cervical cancer in a cervical cancer patient under treatment, methods for predicting the prognosis for a patient with a cervical cancer, methods of predicting efficacy of a treatment of a subtype of cervical cancer in a subject, and methods for selecting patients for treatment with particular therapies and/or therapeutic agents. In some preferred embodiments, the methods, systems and kits are utilized to provide predictive, prognostic, or diagnostic information for particular subtypes of cervical cancers, or to identify patients that are suitable for treatment with particular therapeutic regimens or therapeutic agents.

In some embodiments, the dosage of at least one chromosomal region, or portion thereof (e.g., a gene within the chromosomal region) in a sample is determined. Suitable chromosomal regions include, but are not limited to, 1p36.21-pter, 1p32.1-p34.3, 1q21.1-q22, 3q26.1-qter, 5p15.2-pter, 8q24.13-22, 8q24.3-qter, 9q24.1-2, 9q34.2-qter, 11q22.1-2, 19q13.11-qter, 20q11.21-22, Xp11.22-pter, Xp28-pter, 2q33.3-qter, 3p12.3-p14.2, 4p13-p16.1, 5q13.2, 5q14.2-q15, 6q12-q23.2, 7q34-qter, 8p12-pter, 10q23.31, 11p14.3-pter, 11p12, 11q22.3-qter, 13q12.2-q21.32, 17p11.2-pter, 21q21.1-3, 3p11.2-p14.1, 13q13.1-q21.1, and 21q22.2-3 and combinations thereof. Suitable genes include, but are not limited to, SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK1 HP, FARSB, ACSL3, HRB, SP100, EIF4E2, COPSE, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15.

Determination of the dosage of the foregoing chromosomal regions and genes provides important information for making a number of different clinical diagnoses, prognoses, and predictions. In some embodiments, the alteration in dosage, preferably a decrease in dosage, in said at least one chromosomal region indicates a predisposition to a subtype of cervical cancer cervical cancer. In some embodiments, the alteration in gene dosage indicates that the subject has a subtype of cervical cancer. In some embodiments, the alteration in gene dosage indicates the likelihood of recurrence of cervical cancer. In some embodiments, the alteration in gene dosage indicates poor survival of a patient. In some embodiments, the alteration in gene dosage indicates a prognosis for 60 months survival or more than 60 months survival (e.g., more than 10 year survival or 15 year survival). In another embodiment of the present invention, the prognosis for less than 60 months, such as less than 36 months, such as less than 24 months of survival. In some embodiments, the alteration in gene dosage indicates that the patient is a candidate for treatment with a particular therapy or therapeutic agent. In some embodiments, the alteration in gene dosage indicates the efficacy (e.g., a poor efficacy) of a treatment of a subtype of cervical cancer in a subject.

In some embodiments, the methods further comprise determining the expression level of at least one gene. Suitable genes include, but are not limited to, SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK1 HP, FARSB, ACSL3, HRB, SP100, EIF4E2, COPSE, HDAC4, MTERFD2, PPP1R7, RYBP, GBE1, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, ALG5, FAM48A, COG6, KIAA1704, GTF2F2, MED4, RNASEH2B, SPAG7, MPDU1, LSMD1, CYB5D1, COPS23, ATP5J, RYBP, GBE1, ALG5, FAM48A, COG6, KIAA1704, GTF2F2, MED4, RNASEH2B and PRDM15.

In some embodiments, the alteration in the expression level of the at least one gene relative to a standard expression level of the at least one gene indicates a predisposition to a subtype of cervical cancer cervical cancer. In some embodiments, the alteration in the expression level of the at least one gene relative to a standard expression level of the at least one gene indicates that the subject has a subtype of cervical cancer. In some embodiments, the alteration in the expression level of the at least one gene relative to a standard expression level of the at least one gene indicates the likelihood of recurrence of cervical cancer. In some embodiments, the alteration in the expression level of the at least one gene relative to a standard expression level of the at least one gene indicates poor survival of a patient. In some embodiments, the alteration in the expression level of the at least one gene relative to a standard expression level of the at least one gene indicates a prognosis for 60 months survival or more than 60 months survival (e.g., more than 10 year survival or 15 year survival). In another embodiment of the present invention, the prognosis for less than 60 months, such as less than 36 months, such as less than 24 months of survival. In some embodiments, the alteration in the expression level of the at least one gene relative to a standard expression level of the at least one gene indicates that the patient is a candidate for treatment with a particular therapy or therapeutic agent. In some embodiments, the alteration in the expression level of the at least one gene relative to a standard expression level of the at least one gene indicates the efficacy (e.g., a poor efficacy) of a treatment of a subtype of cervical cancer in a subject.

In some preferred embodiments the subtype of cervical cancer is a subtype of cervical cancer resistant to chemotherapy and/or radiotherapy (radiation therapy/radiation oncology), e.g., a chemoradioresistant cervical cancer.

The identified alterations in gene dosages identified by the inventors (see FIG. 1B) were subjected to survival analysis. The LASSO method (Bovelstad H M et al., 2007) identified three regions with loss of gene dosage, 3p11.2-p14.1, 13q13.1-q21.1, and 21q22.2-3, which jointly showed the strongest association to progression free survival (see Table 2).

Most patients had more than one of the predictive 3p, 13q, and 21q losses. Patients without any of the losses had a low risk of relapse and a survival probability of 91% (see FIG. 2D). Patients with 3p and/or 13q loss, without 21q loss, had an intermediate survival probability of 68%, whereas those with 21q loss had the lowest survival probability of 44%. The risk of relapse therefore is particularly high when loss of 21q22.2-3 was involved.

Accordingly, the invention provides novel loci associated with clinical outcome, providing the first evidence that gene dosage can be responsible for developing chemoradioresistance in cervical cancers, as well as methods, kits and systems that utilize or provide methods for determining the dosage of the novel loci. In some embodiments, the alteration in gene dosage is an increase in gene dosage in said chromosomal region. In another embodiment, the alteration in gene dosage is a reduction of gene dosage in said chromosomal region. In another embodiment of the present invention, the alteration in the expression level of said at least one gene is increased expression of said gene. In another embodiment of the present invention, the alteration in the expression level of said at least one gene is reduced expression of said gene. In some preferred embodiments, the chromosomal region is selected from the group consisting of 3p11.2-p14.1, 13q13.1-q21.1, and 21q22.2-3 and said alteration in gene dosage is a reduction of gene dosage in said chromosomal region. In further preferred embodiments, at least one chromosomal region is the combination of 3p11.2-p14.1 and 21q22.2-3; or 13q13.1-q21.1 and 21q22.2-3; or 3p11.2-p14.1, 13q13.1-q21.1, and 21q22.2-3 and the alteration in gene dosage is a reduction of gene dosage in the chromosomal regions.

In some preferred embodiments, the methods of the present invention determining the gene dosage are combined with further determination of expression level(s) of selected genes, which correlate with the subtype of cervical cancer. In some particularly preferred embodiments, the chromosomal region is 3p11.2-p14.1 and the at least one gene is RYBP and/or GBE1. In some embodiments, the reduction of gene dosage in the chromosomal region correlates with a decrease in the gene copy number of RYBP and/or GBE1. In some preferred embodiments, the chromosomal region 13q13.1-q21.1 and the at least one gene is selected from the group consisting of ALG5, FAM48A, COG6, KIAA1704, GTF2F2, MED4 and RNASEH2B. In some embodiments, the reduction of gene dosage in the chromosomal region correlates with a decrease in the gene copy of at least one gene is selected from the group consisting of ALG5, FAM48A, COG6, KIAA1704, GTF2F2, MED4 and RNASEH2B. In some preferred embodiments, the chromosomal region is 21q22.2-3 and said at least one gene is selected from PRDM15. In some embodiments, the reduction of gene dosage in the chromosomal region correlates with a decrease in the gene copy of PRDM15. In some preferred embodiments, the chromosomal regions are 3p11.2-p14.1, 13q13.1-q21.1, and 21q22.2-3 and the at least one gene is selected from the group consisting of RYBP, GBE1, ALG5, FAM48A, COG6, KIAA1704, GTF2F2, MED4, RNASEH2B and PRDM15. In some preferred embodiments, the methods further comprise obtaining a smoothed ratio using a statistical analysis tool for breakpoint detection.

1. Diagnostic Applications

The present invention provides DNA, RNA and protein based diagnostic methods that either directly or indirectly detect the dosages and/or gene expression levels as described above. The present invention also provides compositions and kits for diagnostic purposes.

The diagnostic methods of the present invention may be qualitative or quantitative. Quantitative diagnostic methods may be used, for example, to discriminate via a cut-off or threshold level. Where applicable, qualitative or quantitative diagnostic methods may also include amplification of target, signal or intermediary (e.g., a universal primer). An initial assay may confirm the presence of a change in gene dosage, but not identify the specific gene. A secondary assay is then performed to determine the identity of the particular gene in which dosage is changed, if desired. The second assay may use a different detection technology than the initial assay.

The dosage of chromosomal regions and/or genes, as well as expression of the genes of the present invention, may be detected along with other markers in a multiplex or panel format. Markers are selected for their predictive value alone or in combination with the identified chromosomal regions and/or genes. Markers for other cancers, diseases, infections, and metabolic conditions are also contemplated for inclusion in a multiplex of panel format.

Any patient sample suspected of containing the gene fusions may be tested according to the methods of the present invention. By way of non-limiting examples, the sample may be tissue (e.g., a cervical biopsy sample), blood, urine, cervical/vaginal secretions or a fraction thereof (e.g., plasma, serum, urine supernatant, urine cell pellet or cervical cells).

The dosage of chromosomal regions and/or genes of the present invention, as well expression of the genes, may be detected using a variety of nucleic acid techniques known to those of ordinary skill in the art, including but not limited to: nucleic acid sequencing; nucleic acid hybridization; and, nucleic acid amplification.

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labelled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labelled primer as you scan from the top of the gel to the bottom.

Dye terminator sequencing alternatively labels the terminators. Complete sequencing can be performed in a single reaction by labelling each of the di-deoxynucleotide chain-terminators with a separate fluorescent dye, which fluoresces at a different wavelength.

Illustrative non-limiting examples of nucleic acid hybridization techniques include, but are not limited to, in situ hybridization (ISH), microarray, and Southern or Northern blot.

In situ hybridization (ISH) is a type of hybridization that uses a labelled complementary DNA or RNA strand as a probe to localize a specific DNA or RNA sequence in a portion or section of tissue (in situ), or, if the tissue is small enough, the entire tissue (whole mount ISH). Examples of suitable ISH methods include, but are not limited to, fluorescence in situ hybridization (FISH), colorimetric in situ hybridization (CISH) or silver in situ hybridization (SISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labelled with either radio-, fluorescent- or antigen-labelled bases is localized and quantitated in the tissue using either autoradiography, fluorescence microscopy or immunohistochemistry, respectively. ISH can also use two or more probes, labelled with radioactivity or the other non-radioactive labels, to simultaneously detect two or more transcripts.

In some embodiments, the dosage of the chromosomal regions and/or genes is detected using FISH, CISH or SISH. Nucleic acid probes specific for the region or gene are labelled with appropriate fluorescent or other markers and then used in hybridizations. The Examples section provided herein sets forth one particular protocol that is effective for measuring deletions but one of skill in the art will recognize that many variations of this assay can be used equally well. Specific protocols are well known in the art and can be readily adapted for the present invention. Guidance regarding methodology may be obtained from many references including: *In situ Hybridization*: Medical Applications (eds. G. R. Coulton and J. de Belleroche), Kluwer Academic Publishers, Boston (1992); *In situ Hybridization*: In Neurobiology; Advances in Methodology (eds. J. H. Eberwine, K. L. Valentino, and J. D. Barchas), Oxford University Press Inc., England (1994); *In situ Hybridization*: A Practical Approach (ed. D. G. Wilkinson), Oxford University Press Inc., England (1992)); Kuo, et al., Am. J. Hum. Genet. 49:112-119 (1991); Klinger, et al., Am. J. Hum. Genet. 51:55-65 (1992); and Ward, et al., Am. J. Hum. Genet. 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

In some embodiments, the dosage of the chromosomal region and/or gene is determined by a microarray based method. Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

In some embodiments, absolute tumor DNA copy numbers is determined by GeneCount, a method for genome-wide calculation of absolute copy numbers from clinical array comparative genomic hybridization data. The tumor cell fraction is reliably estimated in the model. Data consistent with FISH results are achieved. Array comparative genomic hybridization (aCGH) is widely used for genome-wide mapping of DNA copy number changes in malignant cells. Genetic gains and losses impact gene expression levels, and thereby promote tumor growth and progression.

In some embodiments of the present invention, the gene dosage is determined by array comparative genomic hybridization (aCGH). The relative values achieved in aCGH experiments are influenced by the total DNA content (ploidy) of the tumor cells, the proportion of normal cells in the sample, and the experimental bias, in addition to the DNA copy numbers. In another embodiment of the present invention, the gene dosage is the ratio of absolute DNA copy number in said chromosomal regions and the DNA ploidy of the sample. In another embodiment of the present invention, the proportion of normal cells in the sample is estimated and DNA ploidy of the sample is corrected for the presence of normal cells in the sample. In the present context, ploidy refers to the number of complete sets of chromosomes in a biological cell. In humans, the somatic cells that compose the body are diploid (containing two complete sets of chromosomes, one set derived from each parent), but sex cells (sperm and egg) are haploid. In contrast, tetraploidy (four sets of chromosomes) is a type of polyploidy and is common in plants, and not uncommon in amphibians, reptiles, and various species of insects. The number of chromosomes in a single non-homologous set is called the monoploid number (x). The haploid number (n) is the number of chromosomes in a gamete of an individual. Both of these numbers apply to every cell of a given organism. For humans, $x=n=23$; a diploid human cell contains 46 chromosomes: 2 complete haploid sets, or 23 homologous chromosome pairs. The values are presented as intensity ratios between tumor and normal DNA. The data are normalized so that the ratio of 1.0 is the baseline for the analysis, and corresponds to two DNA copies in near diploid (2n) tumors.

In some preferred embodiments, the copy number changes are identified from the ratios deviating from the baseline, using statistical methods for ratio smoothing and breakpoint detection. To assign an absolute copy number to each ratio level identified by the statistical analysis and thereby score genetic aberrations are, however, challenging. In aneuploid tumors with gross alterations in the DNA content, the baseline represents a copy number other than 2, like 3 or 4 in tri- or tetraploid tumors, or a non-integer value when the DNA content differs from n, 2n, 3n, . . . mn. The presence of normal cells within the sample and experimental bias reduce the ratio dynamics. In the present context, euploidy refers to the state of a cell or organism having an integral multiple of the monoploid number, possibly excluding the sex-determining chromosomes. For example, a human cell has 46 chromosomes, which is an integer multiple of the monoploid number, 23. A human with abnormal, but integral, multiples of this full set (e.g. 69 chromosomes) would also be considered as euploid. Aneuploidy is the state of not having euploidy. Moreover, in many tumors, several subpopulations of malignant cells with different genetic characteristics exist, leading to intratumor heterogeneity in the DNA copy numbers and increased complexity in the data. Unreliable results occur, therefore, when common ratio levels are used to score gains and losses in tumors with different ploidy and normal cell content. The confounding effect caused by normal cells within tumor samples is recognized as a problem in aCGH analyses and has been handled by excluding low purity samples or correcting the ratio levels based on histological examination of tumor sections. The latter approach is not satisfactory because only the proportion of connective tissue surrounding the tumor parenchyma, and not the infiltrating immune cells, is precisely quantified. Moreover, the measurements cannot be performed on exactly the same tissue as used in the aCGH experiment and may, therefore, not be representative.

In preferred embodiments utilizing GeneCount, the proportion of normal cells in the sample is estimated and corrected for and possible intratumor heterogeneity in DNA copy numbers is considered. Inputs to the model are the DNA index (DI, where DI=½·tumor ploidy), tumor cell fraction, experimental bias, and aCGH ratios. Predetermined measures of tumor ploidy, determined either by flow or image based cytometry, are useful. The tumor cell fraction can be determined by, for example, flow cytometry on the same part of the sample as used in the aCGH experiment. In cases of unknown normal cell content, the tumor cell fraction is estimated in the model. The experimental bias is determined from the X-chromosome ratio in aCGH experiments where male and female DNA is compared. Smoothed ratio levels from any existing statistical analysis tools for breakpoint detection can be used. The principle of GeneCount is outlined in detail in Lyng et al. (2008).

Current methods for analysis of aCGH data generally score genetic gains and losses based on ratio levels. The breakpoints in individual tumors can be detected with high accuracy by use of statistical algorithms like GLAD and CGH-Explorer. However, the existing downstream analyses, using common ratio levels for scoring aberrations across tumors, fail to identify gains and losses in cases of high ploidy and normal cell content. By the use of GeneCount, the ratio levels are replaced with the absolute copy numbers relative to the total DNA content as measures of gene dosage, which can be compared across tumors regardless of ploidy and normal cell content. The absolute DNA copy number relative to the total DNA content, or gene dosage, is comparable also across tumors.

In some embodiments, the dosage of the chromosomal region and/or gene is determined by Northern or Southern blotting. Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labelled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labelled.

The expression level of a gene as used herein refers to the absolute or relative amount of gene product preferably transcriptional product (RNA) in a given sample. Expressed genes include genes that are transcribed into mRNA and then translated into protein, as well as genes that are transcribed into mRNA, or other types of RNA such as, tRNA, rRNA or other non-coding RNAs, that are not translated into protein. RNA expression is a highly specific process which can be monitored by detecting the absolute or relative RNA levels. Thus, the expression level refers to the amount of RNA in a sample. The expression level is usually detected using microarrays, Northern blotting, RT-PCR, SAGE, RNA-seq, or similar RNA detection methods.

When expression levels of a specific RNA in a test sample is compared to a reference sample they can either be different or equal. However, using today's detection techniques is an exact definition of different or equal result can be difficult because of noise and variations in obtained expression levels from different samples. Hence, the usual method for evaluating whether two or more expression levels are different or equal involves statistics. Statistics enables evaluation of significantly different expression levels and significantly equal expressions levels. Statistical methods involve applying a function/statistical algorithm to a set of data. Statistical theory defines a statistic as a function of a sample where the function itself is independent of the sample's distribution: the term is used both for the function and for the value of the function on a given sample. Commonly used statistical tests or methods applied to a data set include t-test, f-test or even more advanced test and methods of comparing data. Using such a test or methods enables a conclusion of whether two or more samples are significantly different or significantly equal.

In some embodiments, dosage of chromosomal regions and/or genes of the present invention, as well expression of the genes, is detected by an amplification method. Chromosomal regions, genes, and mRNA for expressed genes may be amplified prior to or simultaneously with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPs to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Q-beta replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

Non-amplified or amplified chromosomal regions, genes and mRNA can be detected by any conventional means. For example, the gene fusions can be detected by hybridization with a detectably labelled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

In some embodiments, chromosomal regions, genes or mRNA are detected with a TaqMan assay (PE Biosystems, Foster City, Calif.; See e.g., U.S. Pat. No. 5,538,848 which is herein incorporated by reference). In some preferred embodiments, gene expression is assayed with a TaqMan assay. The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

Oligonucleotide probes of the invention can be synthesized by a number of approaches, e.g. Ozaki et at, Nucleic Acids Research, 20:5205-5214 (1992); Agrawal et at, Nucleic Acids Research, 18:5419-5423 (1990); or the like. The oligonucleotide probes of the invention are conveniently synthesized on an automated DNA synthesizer, e.g. an Applied Biosystems, Inc. Foster City, Calif.) model 392 or 394 DNA/RNA Synthesizer, using standard chemistries, such as phosphoramidite chemistry, e.g. disclosed in the following references: Beaucage and Iyer, Tetrahedron, 48:2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the hybridization efficiencies of the resulting oligonucleotides and/or cleavage efficiency of the exonuclease employed are not adversely affected. Preferably, the oligonucleotide probe is in the range of 15-60 nucleotides in length. More preferably, the oligonucleotide probe is in the range of 18-30 nucleotides in length. The precise sequence and length of an oligonucleotide probe of the invention depends in part on the nature of the target polynucleotide to which it binds. The binding location and length may be varied to achieve appropriate annealing and melting properties for a particular embodiment. Guidance for making such design choices can be found in many of the above-cited references describing the "TaqMan" type of assays.

Preferably, the 3' terminal nucleotide of the oligonucleotide probe is blocked or rendered incapable of extension by a nucleic acid polymerase. Such blocking is conveniently carried out by the attachment of a reporter or quencher molecule to the terminal 3' carbon of the oligonucleotide probe by a linking moiety.

Preferably, reporter molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the reporter by non-radiative decay, the absorption band of the quencher should substantially overlap the fluorescent emission band of the reporter molecule. Non-fluorescent quencher molecules that absorb energy from excited reporter molecules, but which do not release the energy radiatively, are referred to herein as chromogenic molecules.

There is a great deal of practical guidance available in the literature for selecting appropriate reporter-quencher pairs for particular probes, as exemplified by the following references: Clegg (cited above); Wu et al (cited above); Pesce et at, editors, Fluorescence Spectroscopy (Marcel Dekker, New York, 1971); White et at, Fluorescence Analysis: A Practical Approach (Marcel Dekker, New York, 1970); and the like. The literature also includes references providing exhaustive lists of fluorescent and chromogenic molecules and their relevant optical properties for choosing reporter-quencher pairs, e.g. Berlman, Handbook of Fluorescence Sprectra of Aromatic Molecules, 2nd Edition (Academic Press, New York, 1971); Griffiths, Colour and Consitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al, U.S. Pat. No. 3,996,345; Khanna et al, U.S. Pat. No. 4,351,760; and the like.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, reporter and quencher molecules are selected from fluorescein and rhodamine dyes. These dyes and appropriate linking methodologies for attachment to oligonucleotides are described in many references, e.g. Khanna et al (cited above); Marshall, Histochemical J., 7:299-303 (1975); Mechnen et at, U.S. Pat. No. 5,188,934; Menchen et al, European pat. No. application 87310256.0; and Bergot et al, International application PCT/US90/05565. The latter four documents are hereby incorporated by reference.

In some embodiments, expression of the desired gene is assayed by detecting the protein encoded by the gene, preferably by an immunoassay. Illustrative non-limiting examples of immunoassays include, but are not limited to immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldifluoride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counselling based on the results. In some embodiments, the data is used for research use. For example, the data may be used to further optimize the inclusion or elimination of markers as useful indicators of a particular condition or stage of disease.

2. Kits

Compositions for use in the diagnostic methods of the present invention include, but are not limited to, probes, amplification oligonucleotides, and antibodies. Any of these compositions, alone or in combination with other compositions of the present invention, may be provided in the form of a kit. For example, the single labeled probe and pair of amplification oligonucleotides may be provided in a kit for the amplification and detection of gene fusions of the present invention. Kits may further comprise appropriate controls and/or detection reagents. The probe and antibody compositions of the present invention may also be provided in the form of an array.

In still other embodiments, the kits comprise at least one vial containing a control analyte or analytes (such as a genomic sequence). In still other embodiments, the kit comprises instructions for using the reagents contained in the kit for the detection of at least one type of analyte. In some embodiments, the instructions further comprise the statement of intended use required by the U.S. Food and Drug Administration (FDA) in labelling in vitro diagnostic products. The FDA classifies in vitro diagnostics as medical devices and requires that they be approved through the 510(K) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product is placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labelling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination.

3. Drug Screening

In some embodiments, the present invention provides drug screening assays (e.g., to screen for anticancer drugs). The screening methods of the present invention utilize cancer markers identified using the methods of the present invention. For example, in some embodiments, the present invention provides methods of screening for compounds that modulate (e.g., increase or decrease) the expression of cancer marker genes. The compounds or agents may modulate transcription, by interacting, for example, with the promoter region. The compounds or agents may modulate mRNA produced from the fusion (e.g., by RNA interference, antisense technologies, etc.). The compounds or agents may modulate pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention to modulate biological function.

In one screening method, candidate compounds are evaluated for their ability to modulate cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate cancer.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

In one embodiment, an assay is a cell-based assay in which a cell that expresses a cancer marker mRNA or protein or biologically active portion thereof is contacted with a test compound, and the ability of the test compound to the modulate cancer marker's activity is determined Determining the ability of the test compound to modulate cancer marker activity can be accomplished by monitoring, for example, changes in enzymatic activity, destruction or mRNA, or the like.

The ability of the test compound to modulate cancer marker binding to a compound, e.g., a cancer marker substrate or modulator, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radioisotope or enzymatic label to monitor the ability of a test compound to modulate cancer marker binding to a cancer marker substrate in a complex. For example, compounds (e.g., substrates) can be labeled with $^{125}I$, $^{35}S$, $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labelling of any of the interactants can be evaluated. For example, a microphysiometer can be used to detect the interaction of a compound with a cancer marker without the labelling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein, mRNA, or biologically active portion thereof is evaluated. Preferred biologically active portions of the cancer marker proteins or mRNA to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through standard fluorometric detection means well known in the art (e.g., using a fluorimeter).

In another embodiment, determining the ability of the cancer marker protein or mRNA to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labelling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS(N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer markers protein, mRNA, or biologically active portion thereof with a known compound that binds the cancer marker to form an assay mixture, contacting the assay mixture with a test compound, and determining the ability of the test compound to interact with a cancer marker protein or mRNA, wherein determining the ability of the test compound to interact with a cancer marker protein or mRNA includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signalling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

EXAMPLES

Example 1. Gene Dosage, Expression, and Ontology Analysis Identifies Driver Genes in the Carcinogenesis and Chemoradioresistance of Cervical Cancer Integrative analysis of gene dosage, expression, and ontology (GO) data was performed to discover driver genes in the carcinogenesis and chemoradioresistance of cervical cancers. Gene dosage and expression profiles of 102 locally advanced cervical cancers were generated by microarray techniques. Fifty-two of these patients were also analyzed with the Illumina expression method to confirm the gene expression results. An independent cohort of 41 patients was used for validation of gene expressions associated with clinical outcome. Statistical analysis identified 29 recurrent gains and losses and 3 losses (on 3p, 13q, 21q) associated with poor outcome after chemoradiotherapy. The intratumor heterogeneity, assessed from the gene dosage profiles, was low for these alterations, showing that they had emerged prior to many other alterations and probably were early events in carcinogenesis. Integration of the alterations with gene expression and GO data identified genes that were regulated by the alterations and revealed five biological processes that were significantly overrepresented among the affected genes; i.e., apoptosis, metabolism, macromolecule localization, translation, and transcription. Four genes on 3p (RYBP, GBE1) and 13q (FAM48A, MED4) correlated with outcome at both the gene dosage and expression level and were satisfactorily validated in the independent cohort. These integrated analyses yielded 57 candidate drivers of 24 genetic events, including novel loci responsible for chemoradioresistance. Further mapping of the connections between genetic events, drivers, and biological processes suggested that each individual event stimulates specific processes in carcinogenesis through the coordinated control of multiple genes. The present results may provide novel therapeutic opportunities of both early and advanced stage cervical cancers.

Genetic gains and losses; i.e. changes in gene dosages, are common abnormalities of human cancers. Discovering these defects and understanding the biological meaning can lead to improved therapeutic opportunities. This paper reports a large scale screening of gene dosage alterations in cervical cancer and gives a broader exploration of the expression and function of genes with gains or losses. We have focused on the most frequent gene dosage alterations and the alterations associated with survival after chemoradiotherapy, since these defects are likely to be of major importance for developing disease. The most notable finding was the discovery of a set of biological processes that are known hallmarks of cancer and were associated with gains and losses of specific genes. Moreover, novel loci associated with chemoradioresistance independent of existing clinical markers, were found, and the genes involved were depicted. Our results indicated that gene dosage alterations play a causative role in the carcinogenesis and chemoradioresistance of cervical cancer and pinpointed candidate biomarkers of the disease.

Cervical cancer is one of the most common malignancies affecting women worldwide and a major cause of cancer death for women globally. Radiotherapy combined with cisplatin is the treatment of choice at the locally advanced stages. Improved therapy is needed, since more than 30% of the patients show progressive disease within 5 years after diagnosis and treatment related side effects to organs within the pelvis are frequent. Tumor stage, size, and lymph node involvement are the most powerful markers of aggressive disease, but do not fully account for the observed variability in outcome and are not biologically founded. A better handling of the disease may be provided by the discovery of efficient biomarkers for therapeutic planning and intervention, but requires more insight into the mechanisms underlying cervical carcinogenesis and treatment relapse.

During carcinogenesis, genetic and epigenetic alterations drive the evolution of tumor towards increased malignancy and treatment resistance. The changes enable tumor cells to overcome microenvironmental constraints, sustain proliferation, and invade adjacent tissues and distinct organs. Gene dosage alterations like gains and losses regulate the expression of genes and are motive forces for this evolution. Tumor cells bearing an increasing number of gains and losses successively emerge and are selected for based on the growth advantage caused by the genetic changes. Discovery and functional assessment of gene dosage alterations involved in carcinogenesis are therefore essential for understanding the biology of the disease.

At the locally advanced stages of cervical cancer, numerous gene dosage alterations and severe aneuploidy are frequently seen. Moreover, pronounced intratumor heterogeneity in the gains and losses exists within the tumors, reflecting a high genetic instability. The consequences of these alterations for the tumor phenotype are difficult to predict, since large chromosomal regions involving multiple genes are generally affected and some aberrations may be random events without biological significance. Genome wide screening of DNA copy numbers in a decent number of patients enables identification of recurrent gene dosage alterations; i.e., alterations characteristic of the disease, and alterations associated with the clinical outcome, which are likely to be important in carcinogenesis and treatment resistance. Combining the data with expression profiles of the same tumors reveals the genes that are regulated primarily by the genetic events. The potential of this integrative strategy was recently demonstrated in a study on 15 early stage cervical cancers, where genes affected by aberrations on 1q, 3q, 11q, and 20q were reported. Genetic events promoting tumor evolution and treatment resistance have, however, not been explored on a genome wide scale, and their biological meaning has not been addressed.

The present work was conducted to discover candidate driver genes and assess their function in the carcinogenesis and chemoradioresistance of cervical cancers. Genome wide screening of DNA copy numbers and expressions was performed in 102 patients with locally advanced disease. Of these, pairwise data were available for 95 patients. Reliable comparison of gains and losses across the patients was ensured by using the tumor ploidy, as determined by flow cytometry, and the GeneCount method to correct for the normal cell content of the samples and extract the absolute copy numbers and thereby the gene dosages. The use of GeneCount enables mapping of the intratumor heterogeneity in the gene dosage alterations. GeneCount is described in Lyng et al., 2008.

The use of GeneCount also enabled mapping of the intratumor heterogeneity in the gene dosage alterations, providing information of the chronological order in which they had occurred during tumor evolution. The recurrent gene dosage alterations, the alterations associated with outcome after chemoradiotherapy, and the genes that were regulated by these alterations were identified. Further analysis of gene ontology (GO) categories was performed to identify biological processes that were overrepresented among the affected genes and therefore probably regulated by the gene dosage alterations. Such large scale and combined genomic, transcriptional, and functional analysis is powerful in detection of driver genes and their biological meaning, but has not been presented before. We demonstrate the potential of this approach by the identification of five biological processes in carcinogenesis that were associated with recurrent and predictive gains and losses of a set of genes. The set included four genes within the predictive losses for which repressed expression was related to poor outcome in the patient group and in an independent cohort of 41 patients. The genes are candidate drivers of the genetic events and novel biomarkers of cervical cancers.

Results

Recurrent Gene Dosage Alterations.

Figure 6:
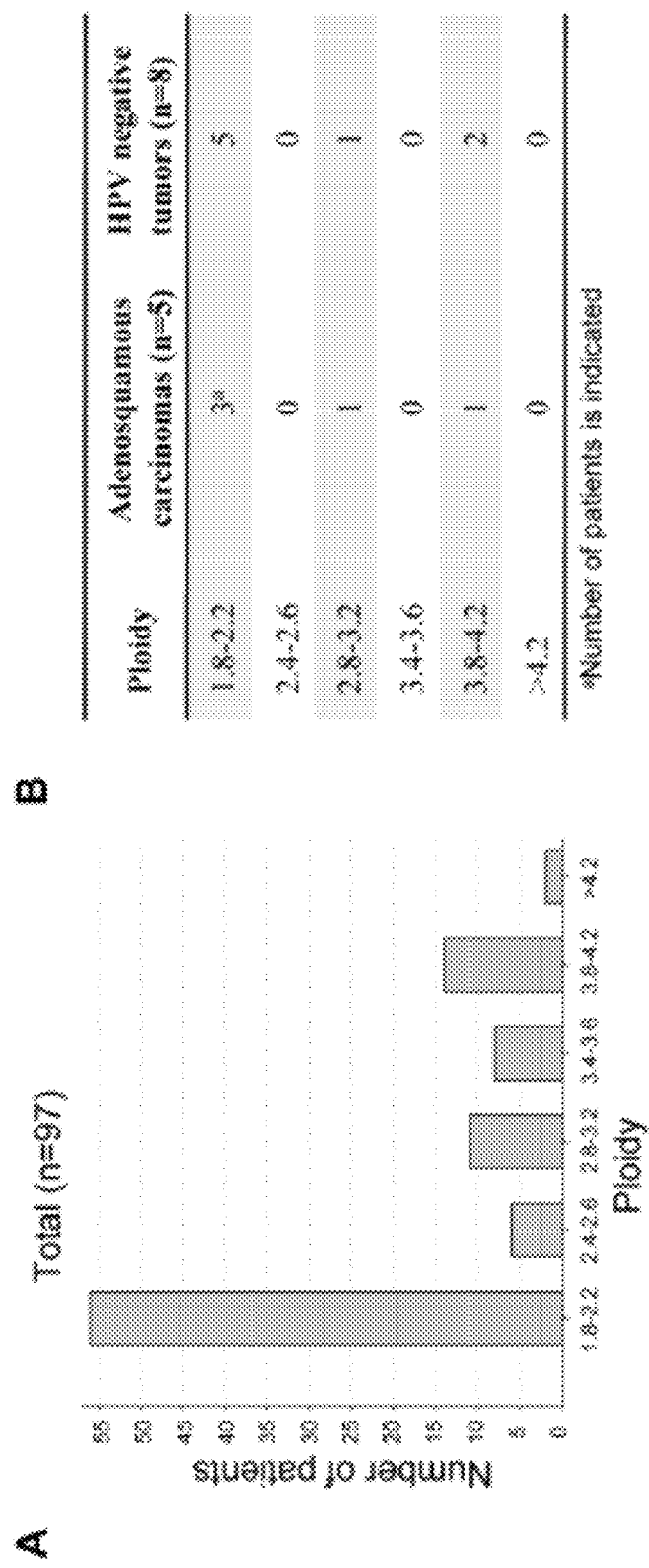
FIG. 6. Tumor ploidy and gene dosage alterations in relation to histological type and HPV status. (A) Ploidy distribution of 97 patients. Tumors with a ploidy within the range of 1.8-2.2 were considered as near diploid. (B) Ploidy of patients with adenosquamous carcinoma or HPV negative tumor. (C, D) Frequency of patients with gains (red) and losses (green) along chromosome 1 to X for patients with adenosquamous carcinoma (C) and HPV negative tumor (D). Gene dosage alterations above 1.1 and below 0.9 were classified as gains and losses, respectively. (A-D) Tumors in the basic cohort subjected to aCGH analysis were included.
Figure 6:
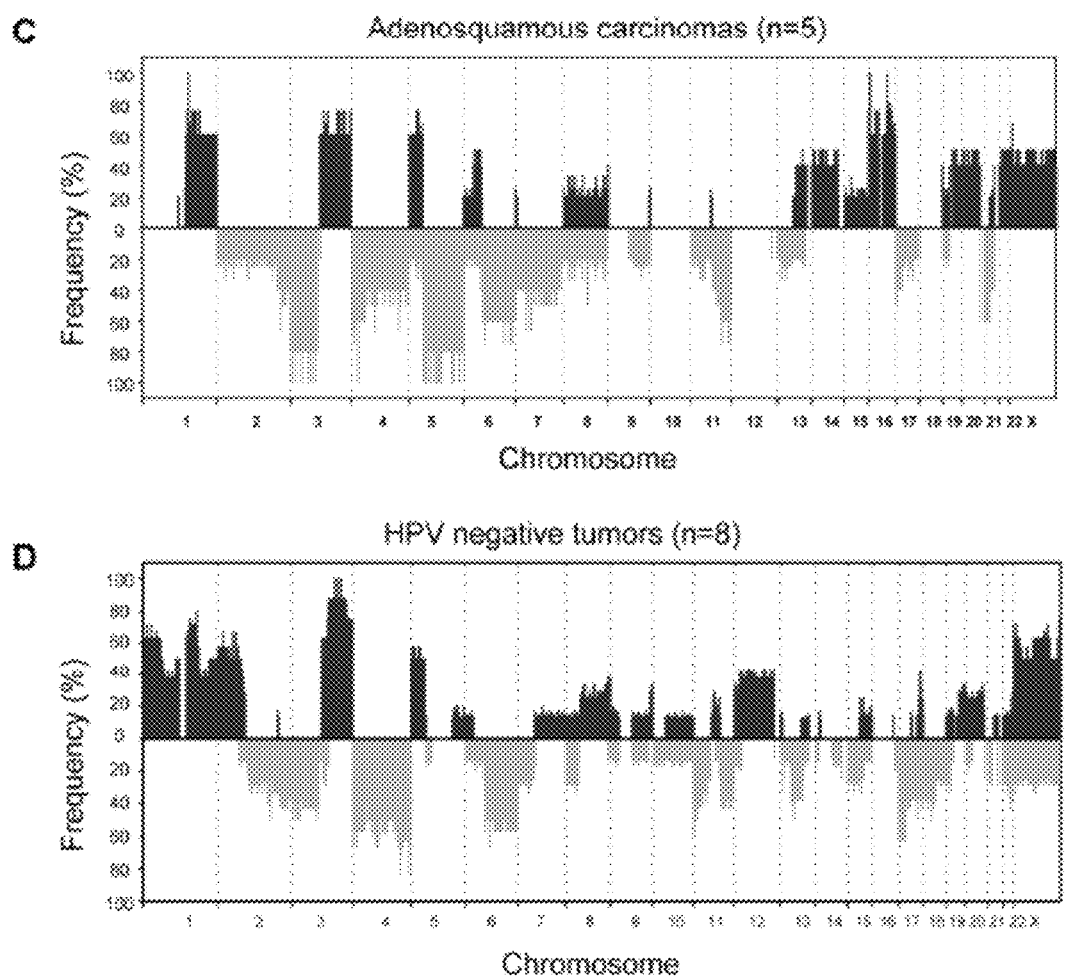

Cervical cancer patients subjected to curative chemoradiotherapy were included in the study (Table 1). Most cases were squamous cell carcinoma and human papillomavirus (HPV) positive. Aneuploidy was seen in about half of the tumors, including some of the adenosquamous carcinomas and HPV negative cases (FIG. 6A, 6B). Based on 97 patients, we generated an absolute gene dosage profile of the cancer genome by the use of array comparative genomic hybridization (aCGH) and the GeneCount analysis tool (FIG. 1A). All chromosomes were affected with gains and losses, however, some regions were more frequently found to be aberrant than others (FIG. 1B). Clustering of the patients based on gene dosages revealed no clear groups with characteristic aberrations.

The recurrent gains and losses were identified by considering both the amplitude and frequency of each alteration in FIG. 1B. Hence, a larger weight was given to high-amplitude events that are less likely to be random aberrations without biological significance. The recurrent alterations comprised more than 42% of the genome, and consisted of 14 regions (528 Mb) with gain and 15 (734 Mb) with loss (FIG. 1C). Most of these alterations were also seen in the adenosquamous carcinomas and the HPV negative tumors (FIG. 6C, 6D). The most common alterations were gain on 1q, 3q, 5p, 20q, and Xq and loss on 2q, 3p, 4p, 11q, and 13q, each involving 44-76% of the patients (FIG. 1C, Table 2). High level amplification (seven regions) and homozygote deletion (six regions) helped to depict the peak of five recurrent gains and two recurrent losses (Table 2, Table 5). The frequency of the homozygote deletions was low (1-3%, Table 5), and none of the tumors had more than one of them. Homozygote alteration is therefore probably not a common mechanism of gene regulation in cervical cancers, in contrast to the highly frequent heterozygote deletion. The highest gene dosage of 36 was found in a diploid tumor with a copy number of 72 on 11q22.1-2 (Table 2).

Intratumor Heterogeneity of the Recurrent Alterations.

Figure 7:
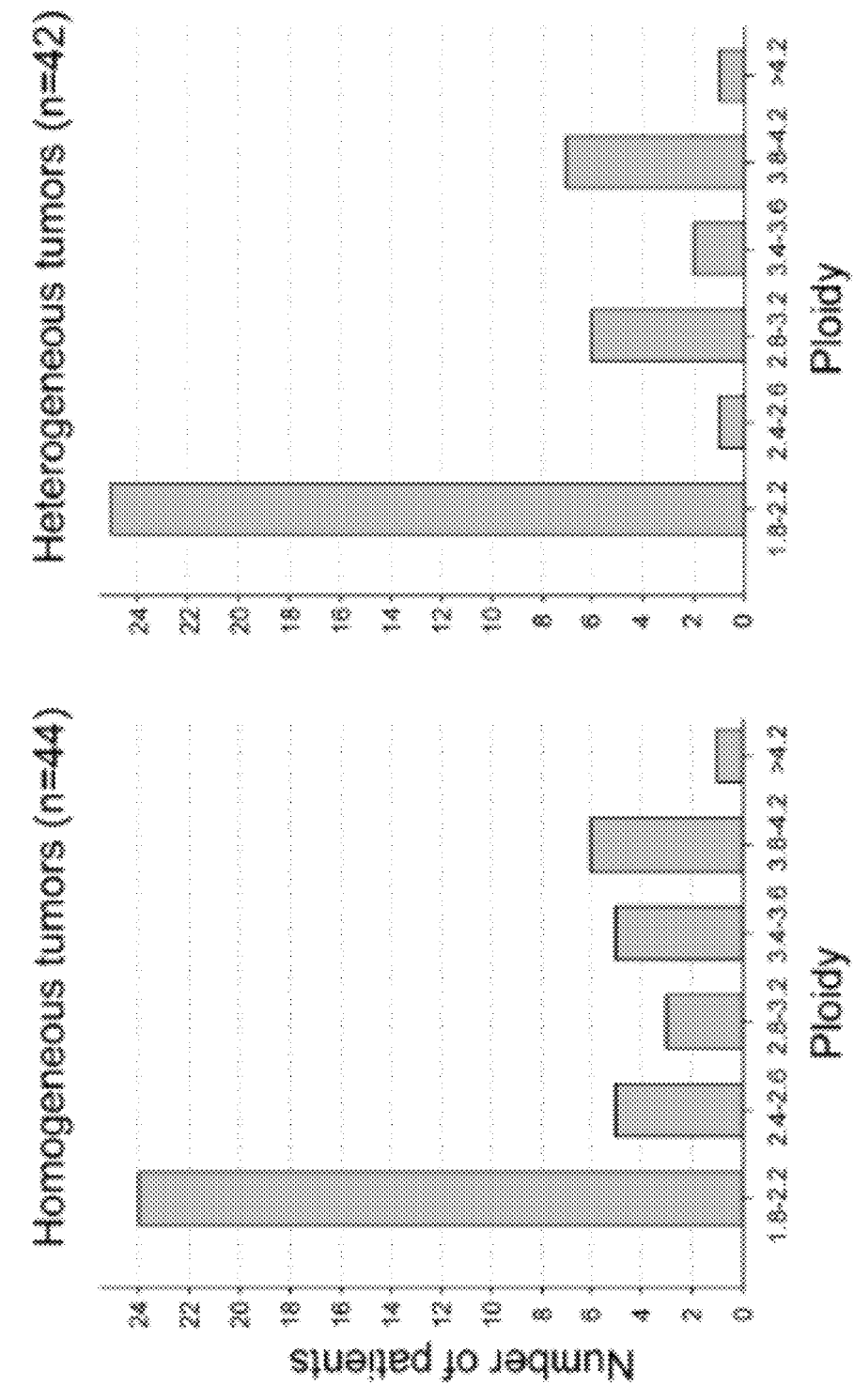
FIG. 7. Tumor ploidy and gene dosage alterations in homogeneous and heterogeneous tumors. (A) Ploidy distribution of patients with homogeneous (left) and heterogeneous (right) tumors. (B,C) Frequency of patients with gains (dark gray) and losses (bright gray) along chromosome 1 to X for patients with homogeneous (B) and heterogeneous (C) tumor. Gene dosage alterations above 1.1 and below 0.9 were classified as gains and losses, respectively. Totally 86 patients with a tumor cell fraction sufficiently high for reliable detection of heterogeneity were included in the analysis.
Figure 7:
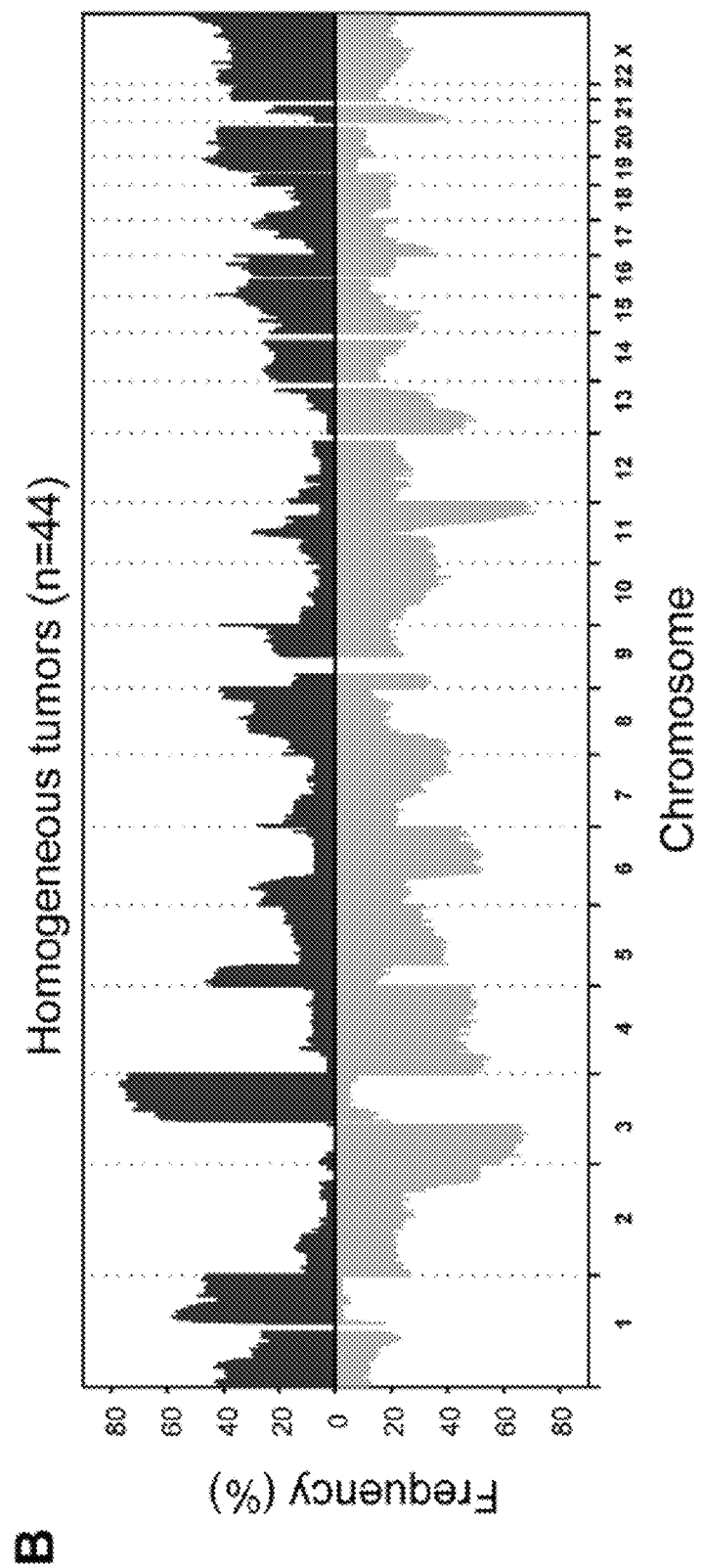
Figure 7:
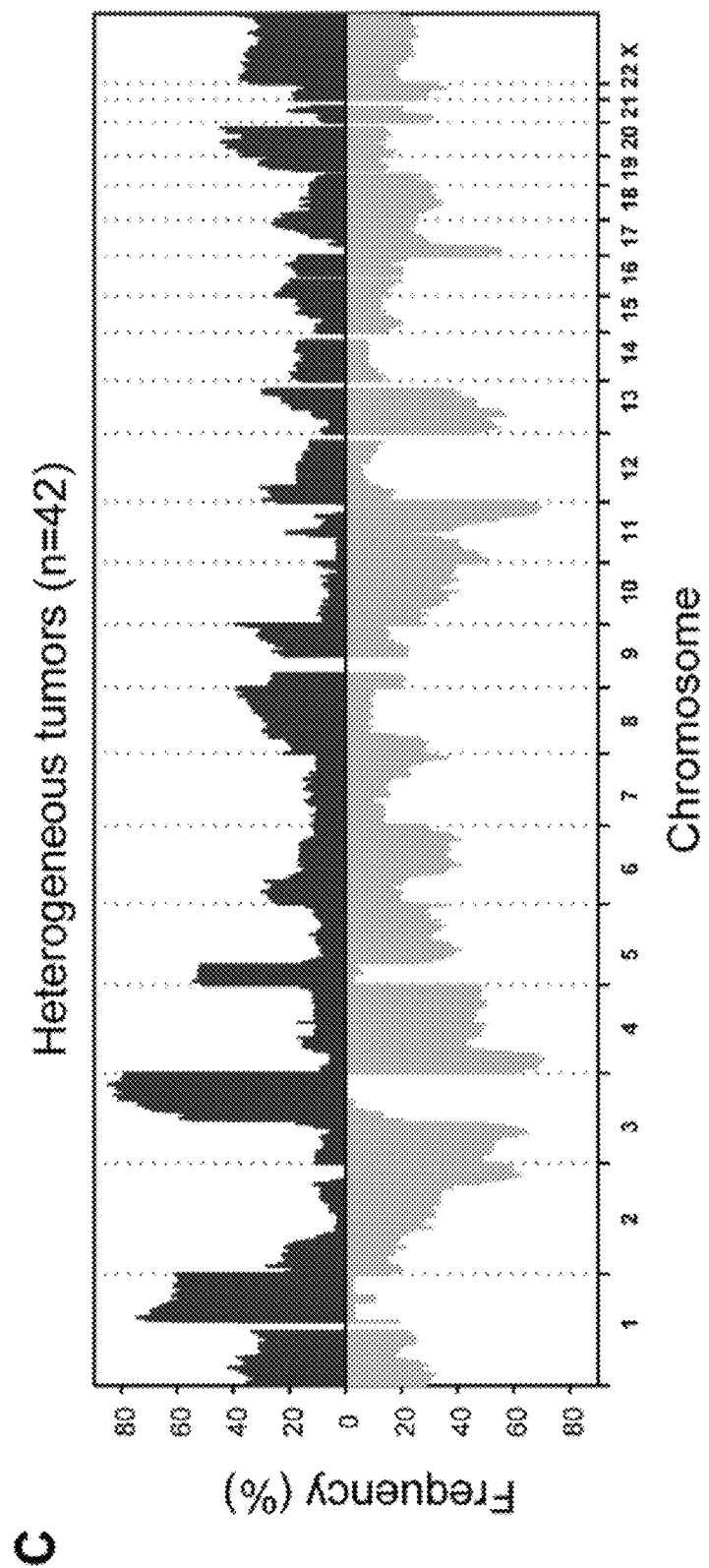

Intratumor heterogeneity in one or more of the gene dosage alterations was seen in about half of the patients. The ploidy and genetic alterations of the heterogeneous tumors were similar to that of the homogeneous ones (FIG. 7). It is reasonable to assume that homogeneous alterations have emerged before the heterogeneous ones during tumor evolution. To order the recurrent alterations chronologically in relation to the less common alterations, we therefore mapped the intratumor heterogeneity along the chromosomes based on the absolute data achieved with GeneCount. The heterogeneity was low for the recurrent alterations compared to others, like gain on 2q and 13q and loss on 1q, 19q, and 20q (FIG. 1D). The recurrent aberrations had therefore probably occurred prior to many of these less common events.

Gene Dosage Alterations in Relation to Outcome after Chemoradiotherapy.

Figure 2:
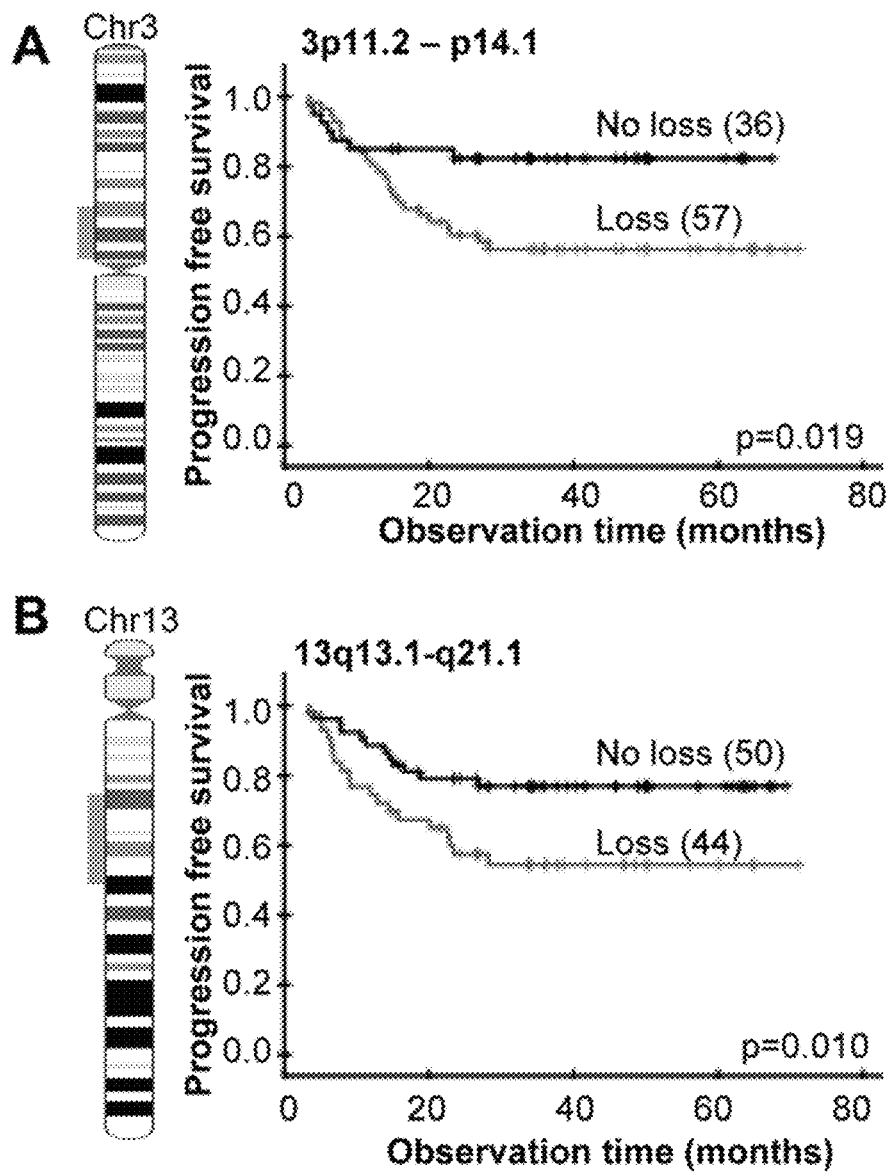
FIG. 2. Gene dosage alterations and outcome after chemoradiotherapy. Kaplan-Meier curves of progression free survival for cervical cancer patients with (gray) and without (black) loss of 3p11.2-p14.1 (A), 13q13.1-q21.1 (B), 21q22.2-3 (C), and for patients with different combinations of the three losses (D). P-values in log-rank test and number of patients are indicated. Data of the most significant genomic clone within each region were used; i.e., BAC clone ID RP11-118O11 (3p), RP11-408L13 (13q), and RP1-128M19 (21q). Total number of patients in (A, B) is less than 97 due to missing gene dosage data. (A-C) The lost DNA region is indicated on the chromosome (left). (D) Group 1: patients without loss of 3p11.2-p14.1, 13q13.1-q21.1, or 21q22.2-3, group 2: patients with loss of 3p11.2-p14.1 and/or 13q13.1-q21.1, but not 21q22.2-3, group 3: patients with loss of 21q22.2-3 only or loss of 21q22.2-3 combined with loss of 3p11.2-p14.1 and/or 13q13.1-q21.1. The groups were determined from data of each possible combination of the losses (FIG. 8).
Figure 2:
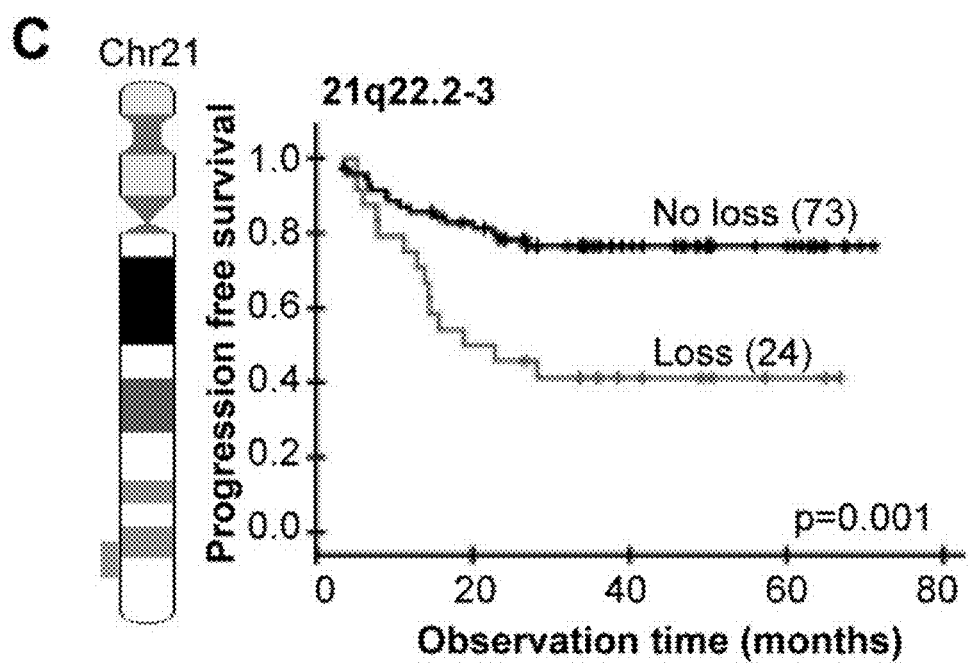
Figure 2:
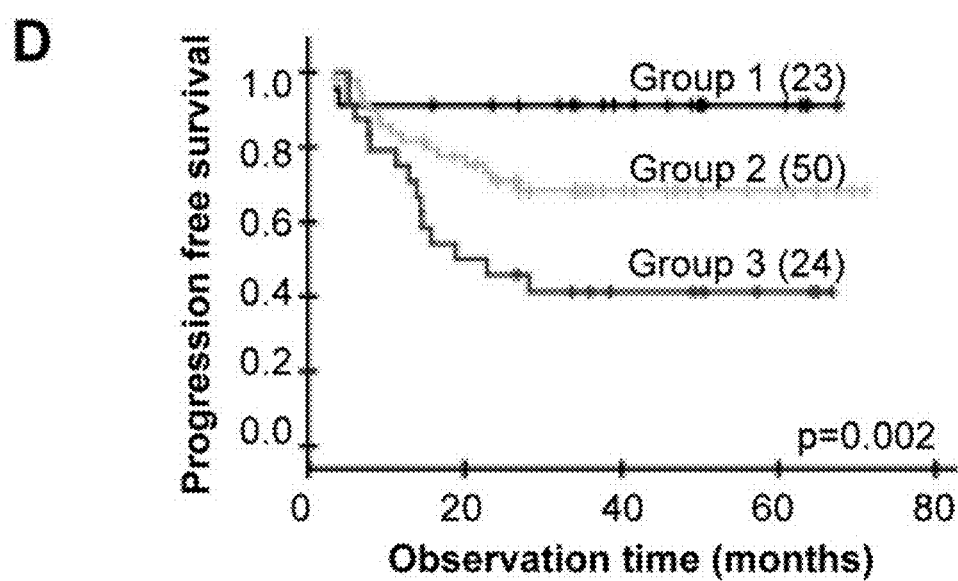

Gene dosage alterations responsible for poor clinical outcome may not be as common as the recurrent ones. All alterations in FIG. 1B were therefore included in the survival analysis. The LASSO method identified three regions with loss, 3p11.2-p14.1, 13q13.1-q21.1, and 21q22.2-3, which jointly showed the strongest association to progression free survival (Table 2). The 3p11.2-p14.1 and 13q13.1-q21.1 regions overlapped with the recurrent 3p12.3-p14.2 and 13q12.2-q21.32 losses, whereas the predictive loss of 21q22.2-3 was distal of the recurrent loss of 21q21.1-3. The predictive losses were not correlated and were related to poor outcome also when analyzed separately (FIGS. 2A-C). The intratumor heterogeneity of the losses was low and similar to that of the recurrent losses (FIG. 1D).

Figure 8:
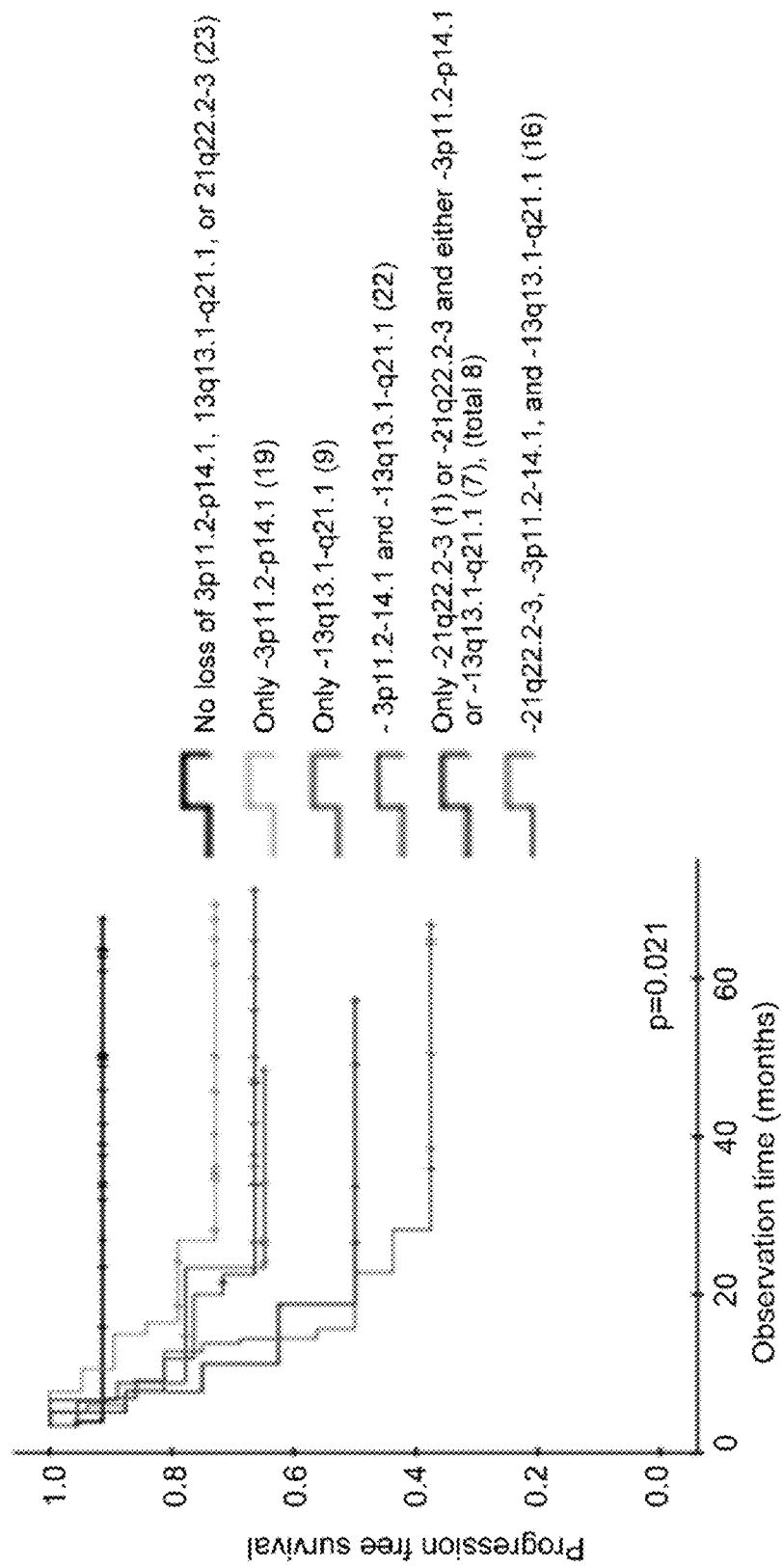
FIG. 8. Clinical outcome for patients with different combinations of predictive losses. Kaplan-Meier curves showing progression free survival after chemoradiotherapy of 97 cervical cancer patients with different combinations of 3p11.2-p14.1, 13q13.1-q21.1, and 21q22.2-3 loss. The different combinations and number of patients in each group are listed (right). P-value in log-rank test is indicated.
Figure 9:
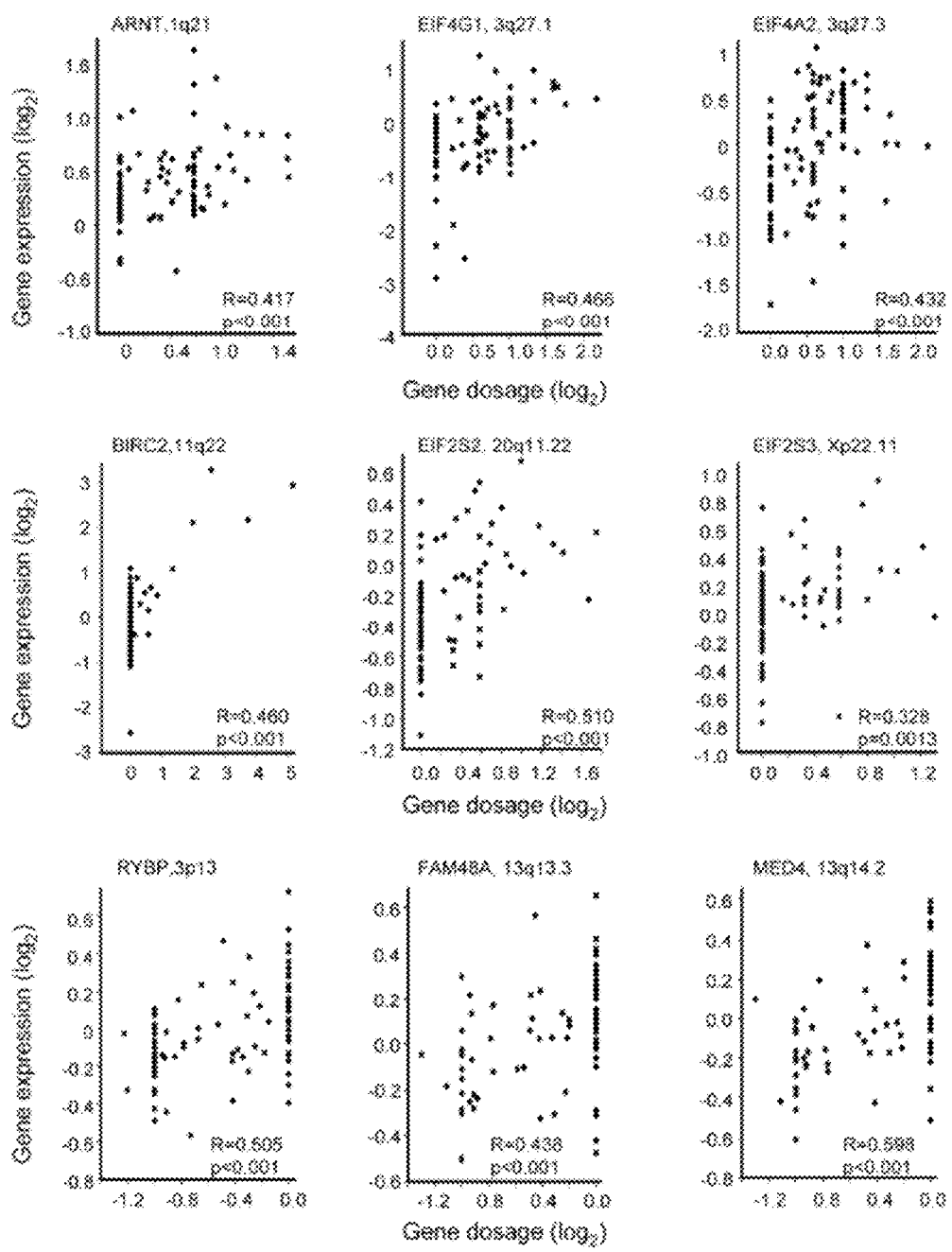
FIG. 9. Correlations between gene dosage and expression. Typical correlation plots of gene dosage and expression for 9 correlating genes within the recurrent and predictive regions; 6 with gain and 3 with loss. Spearman's rank correlation analysis on semi-discrete data was performed, for which amplitudes lower than 1.1 were set to 1 for gains and amplitudes higher than 0.9 were set to 1 for losses. Correlation coefficient (R) and p-value are indicated.

Most patients had more than one of the predictive 3p, 13q, and 21q losses. We therefore investigated whether there was an increased risk of relapse in cases of two or three losses. Kaplan-Meier plots for patients with different combinations of the predictive losses revealed three major groups with different outcome (FIG. 8). Patients without any of the losses had a low risk of relapse and a survival probability of 91% (FIG. 2D). Patients with 3p and/or 13q loss, without 21q loss, had an intermediate survival probability of 68%, whereas those with 21q loss had the lowest survival probability of 44%. The risk of relapse therefore seemed to be particularly high when loss of 21q22.2-3 was involved.

Figure 3:
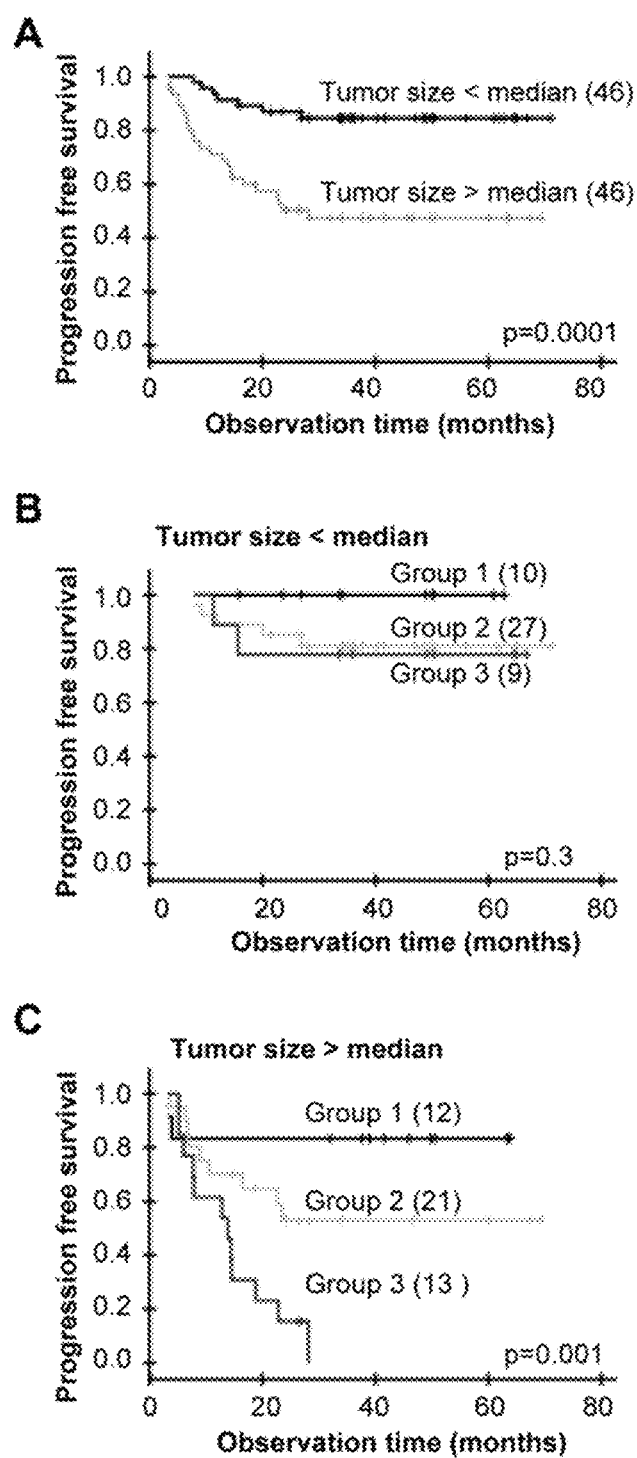
FIG. 3. Gene dosage alterations and outcome after chemoradiotherapy for patients with different tumor size. (A) Kaplan-Meier curves of progression free survival for cervical cancer patients with tumor size above (bright gray) and below (black) median. Ninety-two patients with tumor size determined from diagnostic MR images were included. Median size was 45.1 cm3, corresponding to a diameter of 4.4 cm. (B,C) Kaplan-Meier curves for patients in (A) with tumor size below median (B) and above median (C). Group 1: patients without loss of 3p11.2-p14.1, 13q13.1-q21.1, or 21q22.2-3, group 2: patients with loss of 3p11.2-p14.1 and/or 13q13.1-q21.1, but not 21q22.2-3, group 3: patients with loss of 21q22.2-3 only or loss of 21q22.2-3 combined with loss of 3p11.2-p14.1 and/or 13q13.1-q21.1. The groups were determined from data of each possible combination of the losses (FIG. 8). P-values in log-rank test and number of patients are indicated.

The predictive impact of the 3p, 13q, and 21q losses were assessed by multivariate analysis together with tumor size, stage, and lymph node status. Histological type, HPV status, and heterogeneity status showed no correlation to outcome in univariate analysis and were therefore not included. The losses and tumor size had independent predictive value (Table 3), showing that the gene data contained information of the progression free survival that was not covered by tumor size. Since tumor size is a strong predictor (FIG. 3A), we also investigated the predictive impact of the three losses for small and large tumors separately. About 20% of the patients with tumor size less than the median had relapse and all of them had one or more of the losses (FIG. 3B). In the cases of tumors larger than the median, about 47% of the patients progressed and all except two of them had one or more of the losses (FIG. 3C). None of the patients with loss involving 21q were disease free after 28 months, suggesting a particularly high risk of relapse in cases of a large tumor bearing loss of 21q22.2-3. There was no difference in tumor size for patients with and without loss in FIG. 3B or in FIG. 3C (data not shown). The gene data therefore enabled identification of high and low risk patients both in cases of a small and a large tumor.

Integration of Gene Expression.

To find genes regulated by the recurrent and predictive gene dosage alterations, we used cDNA microarrays and generated a cancer gene expression profile. The profile was based on 100 patients, including 95 of those analyzed with aCGH. Expression data were available for 1357 of the about 4000 known genes within the altered regions, and a significant correlation to gene dosage was found for 191 of them (Table 2). Several correlating genes were identified for each region, except for 8q24.13-22, 10q23.31, and 11p12, where no genes were found. Typical examples of correlation plots are shown in FIG. S4. The results were confirmed with the Illumina gene expression assay on 52 patients. Although the Illumina analysis was based on a lower number of patients, an excellent correlation between the Illumina and cDNA data and between the Illumina and gene dosage data was found for almost all of the genes, as demonstrated in Table S2. We also performed a second cDNA analysis, including only tumors with more than 70% tumor cells in hematoxylin and eosin (HE) stained sections. Totally 179 of the genes (94%) were identified, suggesting few false positive results due to normal cells in the samples. The observations supported our conclusion that the genes in Table 2 were gene dosage regulated. The latter analysis identified 26 genes that were not depicted when all patients were considered. These genes were not considered further, since the results were based on only half of the data set.

Expression of known oncogenes and tumor suppressor genes within the depicted regions, like MYC (8q24.21), BRCA2 (13q13.1), RB1 (13q14.2), and TP53 (17p13.1), was not significantly correlated to gene dosage. These genes are therefore probably not regulated primarily by gains and losses. The TP53 and RB1 results were consistent with the high frequency of HPV positive tumors (Table 1).

Figure 4:
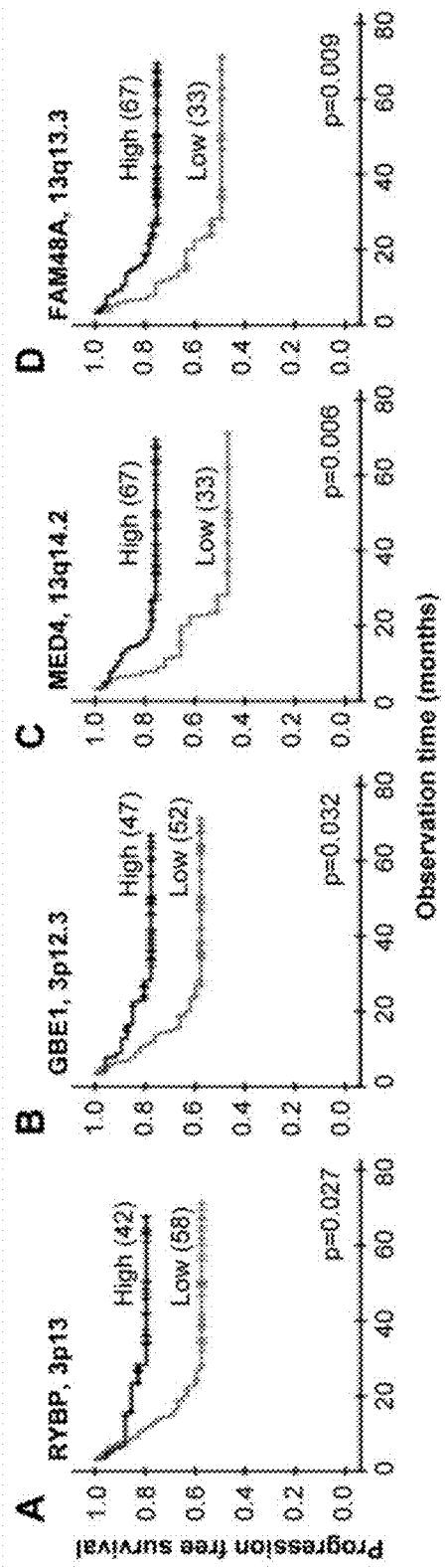
FIG. 4. Gene expressions and outcome after chemoradiotherapy. Kaplan-Meier curves of progression free survival for cervical cancer patients with low (bright gray) and high (black) expression of RYBP (A, E), GBE1 (B, F), MED4 (C, G), and FAM48A (D, H). cDNA data of 100 patients is used in (A-D), and Illumina data of an independent cohort of 41 patients is used in (E-H) for validation. P-value in log-rank test and number of patients are indicated. The number of patients in each group was chosen to achieve the largest difference in survival between the groups, approximately reflecting the number of patients with and without loss in (A-D). Total number of patients is less than 100 in (B) due to missing gene expression data.
Figure 4:
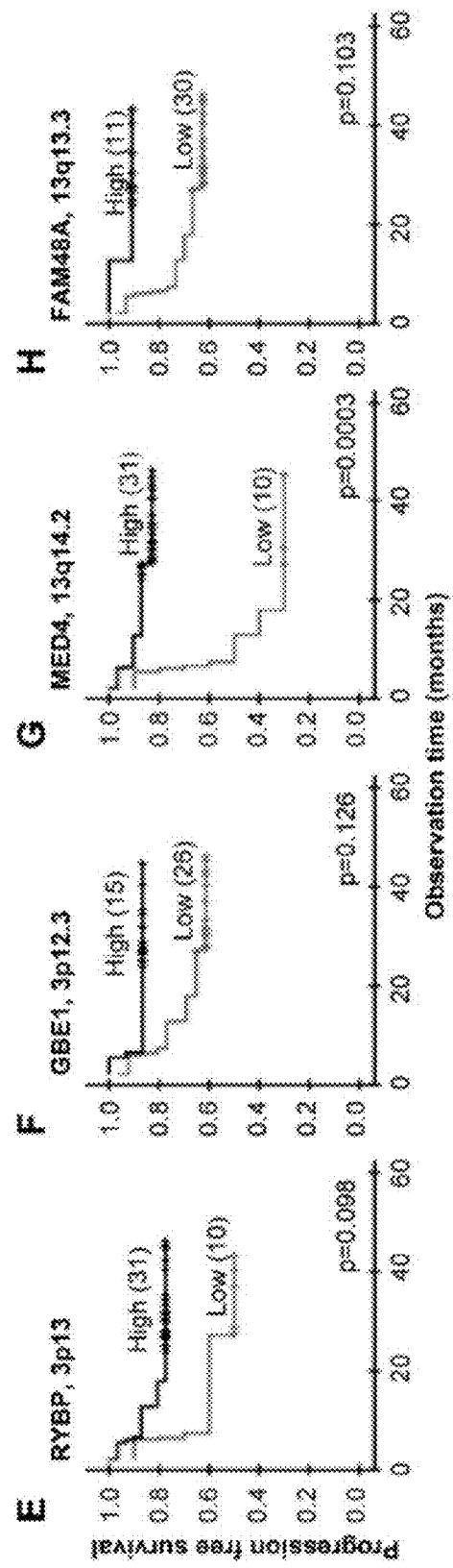

The predictive losses on 3p and 13q involved the same correlating genes as the corresponding recurrent ones, whereas PCP4, RIPK4, and PDXK were correlating genes within the predictive 21q region (Table 2). To depict the correlating genes that most probably were involved in development of chemoradioresistance, we required that the gene was significantly associated with clinical outcome both at the gene dosage and expression level. Moreover, a clear difference in the survival curves should also be seen in an independent cohort of 41 patients when based on the Illumina gene expression data. The criteria were fulfilled for four genes; RYBP and GBE1 on 3p and MED4 and FAM48A on 13q, which were termed predictive genes (FIG. 4). Two more genes, GTF2F2 and RNASEH2B on 13q, were correlated to outcome based on the cDNA data, but were not considered further since the tendency based on the Illumina data was weak (p>0.15). The relationship to outcome was not strong enough for PCP4, RIPK4, and PDXK on 21q to be included among the predictive genes either.

Gene Ontology Analysis.

Biological processes associated with the recurrent and predictive gene dosage alterations were found by comparing the GO categories of the affected genes with those of all genes in the data set. One or more biological processes were annotated to 155 of the correlating and predictive genes and to 5824 of all genes. The categories apoptosis, carbohydrate metabolism, translation, and RNA-protein complex biogenesis and assembly were significantly overrepresented among the correlating genes within the recurrent gains, whereas macromolecule localization, generation of precursor metabolites and energy, transcription from RNA polymerase II promoter, and establishment or maintenance of chromatin architecture were overrepresented among those within the recurrent and predictive losses (Table 4). Fifty-six genes were included in the significant categories and were candidate drivers of the biological processes. In addition, we included the predictive gene FAM48A, which was not associated to any process in the GO database, as a potential driver of chemoradioresistance together with RYBP and MED4 (transcription) and GBE1 (generation of precursor metabolites and energy).

Figure 5:
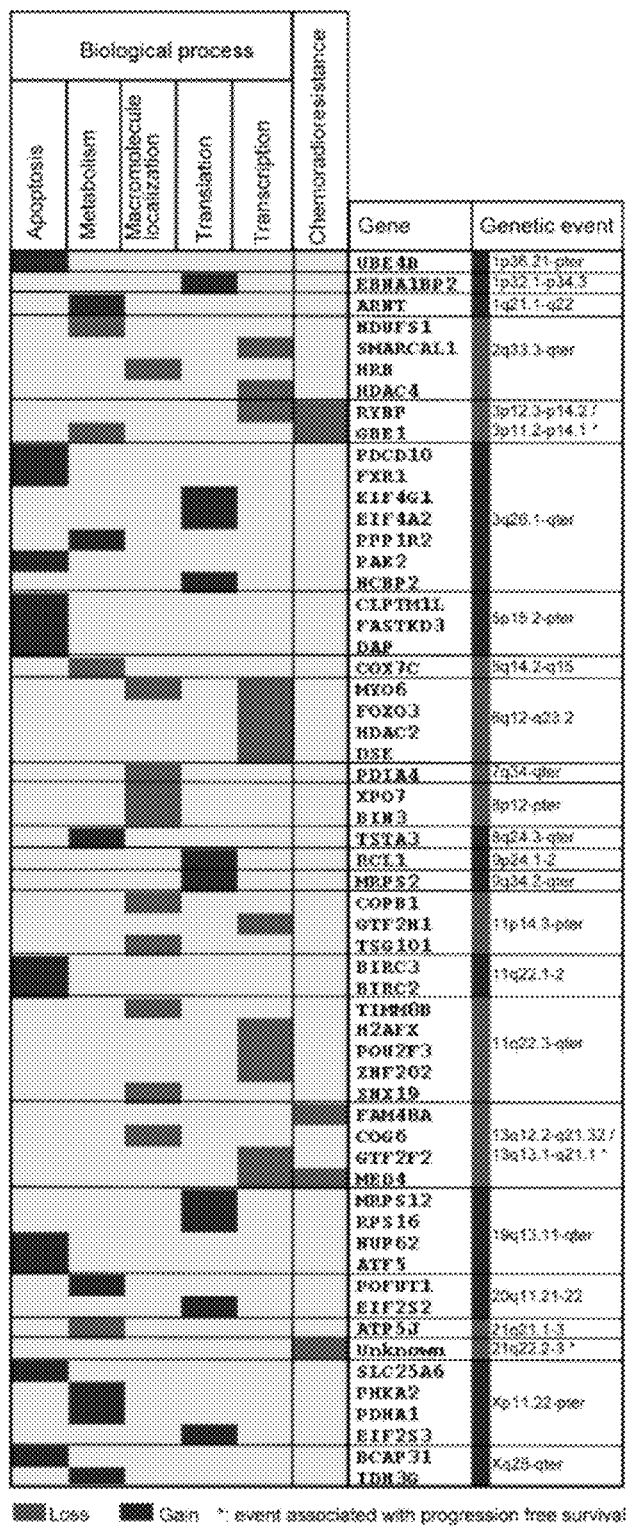
FIG. 5. Genetic events, correlating genes, and biological processes in carcinogenesis and chemoradioresistance of cervical cancers. Recurrent and predictive gene dosage alterations, correlating genes, and biological processes overrepresented among the genes are listed. Only the genetic events associated with a process or chemoradioresistance (*) are included; six of the recurrent alterations are therefore not shown. The genes are ordered by DNA location. Correlating genes connected to chemoradioresistance were associated with clinical outcome both at the gene dosage and expression level and validated in an independent patient cohort. Gains and losses are indicated with dark gray and bright gray color, respectively.

We generated a map to visualize the connections between genetic events, affected genes, and biological processes (FIG. 5). The processes carbohydrate metabolism and generation of precursor metabolites and energy were combined in metabolism, translation and RNA-protein complex biogenesis and assembly were combined in translation, and transcription from RNA polymerase II promoter was combined with establishment or maintenance of chromatin architecture in transcription. The combined categories were closely related, justifying this strategy. All but six of the recurrent alterations were associated with a process and represented in the map. The predictive 3p and 13q losses were merged with the corresponding recurrent losses, since the regions overlapped, and linked to metabolism (GBE1) and transcription (RYBP, MED4) in addition to chemoradioresistance. The predictive 21q loss was not connected to any known gene, but associated with chemoradiosistance. The map revealed features that seemed to be characteristic of recurrent and predictive alterations in cervical cancer. First, many of the genetic events were associated with clusters of genes in the same biological process. For example, gain on 3q affected three genes in apoptosis and three in translation, gain on 5p was linked to tree apoptosis genes, and loss on 6q was associated with four genes in transcription. Second, several events, like gain on 3q, 19q, 20q and loss on 2q, 6, and 11q, were connected to more than one biological process, either through the regulation of several genes or because some genes had multiple functions.

Discussion

This work presents the first coupling of gene dosage and expression profiles in a large sample set of cervical cancers. We based our study on absolute gene dosages, which are more sensitive than the commonly used aCGH ratios in detecting gains and losses and enable comparisons across tumors with differences in ploidy and normal cell content. This strategy and the large number of patients ensured reliable identification of recurrent gene dosage alterations, events associated with clinical outcome, and their intratumor heterogeneity. Further analysis based on GO categories provided an objective way of organizing the numerous correlating genes into biological meaningful information. We demonstrate a large potential of the integrative approach by the discovery and functional assessment of candidate driver genes that represent novel biomarkers of the disease. In particular, novel loci associated with clinical outcome were identified, providing the first evidence that gene dosage can be responsible for developing chemoradioresistance in cervical cancers.

The recurrent gene dosage alterations were consistent with earlier reports on advanced stage cervical cancer based on conventional CGH. However, a more precise definition of the altered regions was achieved here due to the improved resolution of the array technique. The high frequency of the alterations suggests that they play a causative role in carcinogenesis. Hence, many of the alterations are common also in other squamous cell carcinomas, like head and neck cancers. Moreover, the recurrent loss on 3p and 13q overlapped with the losses associated with poor clinical outcome, strengthening the hypothesis of a central role in tumor evolution. Less frequent alterations can, however, also be crucial for tumor evolution, as was demonstrated by the recurrent gain on 11q22 in 14 patients and predictive loss on 21q in 23 patients.

The low intratumor heterogeneity of the recurrent and predictive gene dosage alterations indicated that they had occurred prior to many of the other alterations. The result was consistent with our previous cervical cancer study based on conventional CGH, showing a homogeneous intratumor distribution of the frequent gains on 3q, 5p, and 20q and losses on 3p and 11q14-qter. Moreover, regions overlapping with the 1p, 1q, 3q, 8q, 9q, and 20q recurrent gains and 2q, 3p, 4p, 11q, and 17p losses have been found to be altered in precancerous cervical intraepithelial lesions, suggesting that the events had occurred at an early stage. It is therefore likely that the alterations identified here, and the consequently control of biological processes and development of chemoradioresistance, emerge early during carcinogenesis. It should be noted that a low heterogeneity was seen for some of the less common alterations as well, implying that they had occurred early. The affected genes in these regions may also be crucial for tumor evolution, however, other mechanisms than gene dosage alterations, such as epigenetic events or mutations, probably play the major role in their regulation. Moreover, some of the highly heterogeneous alterations may be important for disease progression a later stage, being a result of the continuing tumor evolution towards increased aggressiveness.

The gene dosage alterations were associated with specific biological processes that are closely related to known cancer hallmarks, indicating that the genes involved are drivers of carcinogenesis. Hence, gain of the genes in apoptosis, including the anti-apoptosis genes BIRC2, BIRC3, and ATF5, can help carcinoma cells to evade apoptosis. Aberrations of the genes in metabolism, like gain of ARNT and IDH3G in carbohydrate metabolism, and loss of COX7C and ATP5J in oxidative phosphorylation, can be part of a metabolic reprogramming towards increased glycolysis and decreased mitochondrial function to meet the high energy demand linked to tumor growth. In particular, gain of ARNT may increase hypoxia and hypoglycemia tolerance by signalling through the HIF1A pathway. Loss of the genes in molecular localization, including HRB and TSG101, can lead to abnormal protein internalization and recycling and thereby abrogated degradation of proteins like growth factor receptors. Finally, aberrations of the genes in translation and transcription, such as gain of the translation initiation factors EIF4A2, EIF4G1, EIF2S2, and EIF2S3 and loss of the transcriptional repressors HDAC2 and HDAC4, can be a way to control the formation and activity of essential proteins. The EIF-proteins are central in adaptation to hypoxia and can stimulate MYC translation and thereby oncogenic processes like cell proliferation. Improper function of HDAC2 and HDAC4 may also increase proliferation. Many of the genes, including BIRC2, BIRC3, ATF5, NUP62, FASTKD3, IDH3G, and POFUTI, have been found to be regulated by gains or losses in previous cervical cancer studies. Our findings link each gene to one or more specific biological processes, and thereby indicate the functional meaning of the genetic events in carcinogenesis.

Loss and down regulation of GBE1 and RYBP on 3p and MED4 and FAM48A on 13q were associated with poor clinical outcome, suggesting that the genes are drivers of chemoradioresistance. The mechanisms underlying these findings and possible associations to known aggressive phenotypes like hypoxia and rapid proliferation are not clear, but a tumor suppressor function of the genes has been indicated. GBE1, which plays a role in carbohydrate metabolism, has been found to be down regulated in ovarian cancers. Loss of the transcriptional repressor RYBP may impair death receptor-mediated apoptosis, and the encoded protein has been shown to be down regulated in many tumor types, including cervical cancer. Loss of the transcriptional activators MED4 may impair transcription of genes with anti-cancer effect, like the vitamin D receptor. The function of FAM48A is less clear, but some studies indicate that loss of this gene can promote aggressiveness. Hence, FAM48A is required for activation of the MAPK p38 pathway, which represses cell proliferation. We found no candidate driver gene of chemoradioresistance within the predictive loss on 21q. Only a few tumor suppressor genes have been identified in this region. One candidate is the transcriptional regulator PRDM15, which was not included in our cDNA data set. Our data showed, however, no correlation between PRDM15 expression, assessed with the Illumina method in 52 patients, and gene dosage (data not shown), suggesting that the gene is not regulated by genetic loss. Further investigation with denser microarrays or possibly microRNA screening would be needed to find the drivers in this region.

The connection between genetic events, genes, and biological processes may provide insight into more general aspects of cervical carcinogenesis. Several genes were often associated with a single genetic event, supporting the hypothesis that there can be multiple drivers of an event that coordinately promote tumor evolution. In cases of genes in the same biological process, like the anti-apoptosis genes BIRC2 and BIRC3 on 11q22, a broad and therefore efficient control of the process may be obtained. Hence, BIRC2 and BIRC3 may play complementary roles in apoptosis evasion, since upregulation of BIRC3, but probably not BIRC2, may impair hypoxia induced apoptosis. In cases of genes in different biological processes, such as metabolism (NDUFS1), macromolecule transport (HRB), and transcription (SMARCAL1, HDAC4) on 2q, the collective control of these processes through a single event is likely to give a growth advantage that is selected for in carcinogenesis. One or more genes in all biological processes were affected in most tumors due to the high frequency of the recurrent gene dosage alterations. All processes were therefore probably important, and the control of them through gains and losses seems to be a common feature of the disease.

The candidate driver genes represent novel biomarkers that may be utilized in the handling of cervical cancers. Diagnostic assessment of the biomarkers may help to understand the evolutionary status and therefore the biology of the cancer in individual patients. In particular, the predictive biomarkers may be used in addition to tumor size for classification of patients into risk groups in a personalized treatment regime. The biomarkers also open for the possibility to specifically repress biological processes in carcinogenesis by molecular targeting, and thereby interfere with tumor evolution. The use of drugs to inhibit translation by interaction with EIF-proteins has shown promising results and been suggested as a tool to target tumor hypoxia. The approach may be applied at all stages of the disease, since the genetic events probably emerge early. Moreover, improved outcome after chemoradiotherapy might be achieved by targeting the predictive biomarkers. Hence, viral-mediated delivery of RYBP has been shown to induce apoptosis in a number of cancer cell lines, and could be a useful strategy for the patients with loss of this gene.

Materials and Methods

Patients.

A cohort of 102 patients was included for basic analyses to identify gene dosage alterations with aCGH (97 patients), affected transcripts with cDNA microarrays (100 patients), and to confirm the affected transcripts with the Illumina method (52 patients) (Table 1). An independent cohort of 41 patients was used to validate relationships between gene expression and outcome with the Illumina method (Table 1). All patients received external irradiation and brachytherapy combined with adjuvant cisplatin and were followed up as described previously. Eighteen patients received extended radiation field due to enlarged common iliac and para-aortal lymph nodes. Progression free survival, defined as the time between diagnosis and the first event of locoregional and/or distant relapse, was used as end point. Six patients died of causes not related to cancer and were therefore censored. Tumor samples were collected at the time of diagnosis. One-four biopsies, approximately 5×5×5 mm in size, were taken at different locations of the tumor, immediately snap-frozen in liquid nitrogen and stored at −80° C. until used for analyses. The study was approved by the regional committee of medical research ethics in southern Norway, and written informed-consent was achieved from all patients.

Array Comparative Genomic Hybridization.

The aCGH experiments and generation of absolute gene dosage profiles have been described previously for all 97 patients (ArrayExpress accession no. E-TABM-398). The array slides were produced at the Microarray Facility at the Norwegian Radium Hospital and contained 4549 unique genomic BAC and PAC clones that covered the whole genome with a resolution of approximately 1 Mb. Genomic DNA was isolated from the biopsies, labeled, and co-hybridized with normal female DNA to the array slides. DNA from different biopsies of the same tumor was pooled. The biopsies of all except two patients had more than 50% tumor cells in HE stained sections from the middle part of the sample. Median tumor cell fraction was 70% (range 30-90%). After array scanning, image analysis, spot filtering, and ratio normalization, the GLAD algorithm was applied for ratio smoothing and breakpoint detection.

Absolute Gene Dosages.

The smoothed ratios were transferred to absolute DNA copy numbers in GeneCount by utilizing tumor ploidy data and correcting for the normal cell content of the samples. The tumor ploidy was determined from a separate piece of the biopsy by flow cytometry, and tumor cell fraction was estimated by the program prior to the copy number calculations. The ploidy data and tumor cell fractions have been presented previously. The tumor cell fractions, ranging from 27% to 84%, were in general lower than the results based on HE stained sections, probably because the amount of immune cells infiltrating the tumor parenchyma are difficult to quantify by histological examination. The copy numbers were rounded off to the nearest integer values.

The absolute gene dosage profile of each tumor was generated by dividing each copy number by the ploidy. A gene dosage of 1 therefore implied no change in the copy number. The gene dosage thresholds for scoring gains and losses were 1.1 and 0.9, respectively, taking into account an uncertainty in the ploidy measurement of approximately 10%. For scoring high level amplification, a gene dosage of 2.5 or higher; i.e. 5 DNA copies in diploid tumors, was required. Homozygote deletions had a gene dosage of 0.

Intratumor Heterogeneity.

The intratumor heterogeneity in the copy numbers was assessed by comparing the aCGH ratio distributions of the possible heterogeneous regions with the distributions of the adjacent homogeneous regions by ANOVA analysis. Totally 86 patients had a tumor cell fraction sufficiently high for reliable detection of heterogeneity, and the remaining eleven patients were excluded from this analysis. The heterogeneous regions have been listed previously. A heterogeneity index was calculated for gains and losses separately, as the number of heterogeneous cases relative to the total number of cases with alteration at each DNA location. The copy number of the heterogeneous region was 0.5 above (gain) or below (loss) the nearest integer value.

The GeneCount method has been extensively validated based on the cervical cancer samples included in this study and a cohort of 94 lymphoma samples. In particular, we used lymphoma samples to show that the estimated tumor cell fractions correlate significantly with the highly accurate values determined by flow cytometry.

cDNA Microarrays.

The cDNA microarray experiments have been presented previously for 48 of the 100 patients. The array slides were produced at the Microarray Facility at the Norwegian Radium Hospital and contained more than 12000 unique cDNA clones, including most known oncogenes and tumor suppressor genes. Total RNA was isolated from the biopsies, labeled, and co-hybridized with reference RNA (Universal Human Reference RNA, Stratagene, La Jolla, Calif.) to the array slides. RNA from different biopsies of the same tumor was pooled. Only biopsies with more than 50% tumor cells in HE stained sections were utilized. Median tumor cell fraction was 70% (range 50-90%). All hybridizations were performed twice in a dye-swap design (ArrayExpress accession no. E-TABM-817). After array scanning, image analysis, spot filtering, and ratio normalization, the average expression ratios were calculated from the two data sets and used in the further analyses. The gene expressions were mapped to the gene dosages based on the exact chromosomal position of the cDNA and genomic clones, as derived from Ensembl.

Illumina Gene Expression Beadarrays.

Results based on cDNA data were validated with Illumina gene expression beadarrays in 52 of the patients subjected to aCGH and in the independent cohort of 41 patients. HumanWG-6 v3 beadchips (Illumina Inc., San Diego, Calif.) with 48000 transcripts were used. RNA was isolated from the biopsies as described above and amplified using the Illumina® TotalPrep RNA amplification kit (Ambion Inc., Austin, Tex.) with 500 ng of total RNA as input material. cRNA was synthesized overnight (14 hr), labelled, and hybridized to the chips at 58° C. overnight, according to the standard protocol. The hybridized chip was stained with streptavidin-Cy3 (Amersham™, PA43001, Buckinghampshire, UK) and scanned with an Illumina beadarray reader. The scanned images were imported into BeadStudio 3.1.3.0 (Illumina Inc.) for extraction, quality control, and quintile normalization. The annotation file HumanWG-6_V3_0_R0_11282955_A was used.

Statistics.

The recurrent gene dosage alterations were identified based on a score that was calculated for each genomic clone by multiplying the average gene dosage amplitude with its frequency. Gains and losses were considered in two separate procedures. Semi-discrete data were used, for which amplitudes lower than 1.1 were set to 1 when searching for gains and amplitudes higher than 0.9 were set to 1 when searching for losses. The score significance was assessed by comparison to similar scores obtained after data permutation, adjusting the p-value by a multiple testing procedure to control the false discovery rate (FDR). Recurrent alterations with an FDR q-value<5% were reported.

Gene dosage alterations associated with clinical outcome were identified with the LASSO method in the Cox proportional hazards model. The LASSO is a method for variable selection and shrinkage in regression models when the number of covariates is larger than the number of individuals. By performing shrinkage in addition to selection, the LASSO is more stable than stepwise procedures where variables are either retained or discarded from the model sequentially, one at a time. In groups of highly correlated variables the LASSO tends to select only one variable in the group, and reported therefore one representative of each DNA region that jointly explained the outcome. Each region was thereafter found by selecting neighbouring genomic clones with strong correlation (r>0.9) to the one reported. Survival curves were generated by Kaplan-Meier analysis and compared by using log-rank test.

Spearman's rank correlation analysis with an FDR q-value<5% was used to search for significant correlations between gene dosage and expression. The analysis was based on semi-discrete data, retrieved as described above. To identify biological processes that were overrepresented among the correlating genes, the GO categories of the genes were compared with those of all genes on the array by using the master-target procedure with the Fisher's exact test in the eGOn software. The GO categories were found in eGOn from public databases, based on the gene reporter Entrez-GeneID.

Example 2. Integrated Genomic and Transcriptional Profiling of Cervical Cancers Reveals Candidate Biomarkers of Chemoradioresistant Disease Purpose.

Gene dosage alterations like gains and losses influence gene expressions and are motive forces for tumor development and progression. The purpose of this work was to identify gene dosage alterations and the affected transcripts in locally advanced cervical cancers, and explore their role in development of chemoradioresistant disease.

Materials and Methods.

A total of 102 patients with locally advanced squamous cell carcinoma of the uterine cervix were included. All patients received radiotherapy with or without cisplatin. Tumor biopsies were taken before the start of treatment and used for the molecular profiling. Gene dosage and expression profiling was performed by array comparative genomic hybridization (aCGH) and cDNA microarray analysis, respectively. Pairwise data were available for 95 patients. The GISTIC and LASSO methods, suitable for statistical analysis of large scale data, were applied to identify recurrent gene dosage alterations and alterations associated with clinical outcome, respectively. Correlations between gene dosage and expression were searched for by Spearman's rank correlation analysis with multiple testing correction, requiring a false discovery rate of <5% for significance.

Results.

The recurrent gene dosage alterations comprised more than 42% of the human genome, for which 528 Mb were gains and 734 Mb were losses. A significant correlation between gene dosage and expression was found for more than 260 genes located within the regions with recurrent alteration. Many of the genes with the strongest correlation and therefore probable targets for the genetic events, were known to be involved in tumor cell survival, proliferation and hypoxia response. The most frequent gain occurred on 1q21-22 and 3q26-ter, affecting 60% and 72% of the tumors, respectively. ARNT (HIF1) (1q21), EIF4A2 (3q28) and EIF4G1 (3q27), playing a role in translational control under hypoxia, were among the overexpressed genes within these regions. Other members of the EIF-family within the frequently amplified regions on 20q and Xp, EIF2S2 (20q11) and EIF2S3 (Xp22), were also highly upregulated. The recurrent losses strongly affected genes that promote apoptosis, hypoxia induced cell death and cell cycle arrest, like RYBP (3p13), BNIP3L (8p21) and CHEK1 (11q24.2), respectively. The relationship to clinical outcome was stronger for losses than for gains. We identified three deleted regions on 3p14-cen, 13q13-21, and 21q22, which were independently associated with poor progression free survival. Five genes within these regions, RYBP (3p13), MED4 (13q14.2), GTF2F2 (13q14), FAM48A (13q13.3) and RNASEH2B (13q14.3), were significantly downregulated and associated with progression free survival at the transcriptional level, supporting the hypothesis that they are target genes for the losses.

Conclusion.

Integrated analysis of gene dosages and expressions revealed novel candidate oncogenes and tumor suppressor genes important for cervical cancer progression. Gene dosage alterations probably play an important role in the development of chemoradioresistant phenotypes. Moreover, the high frequency of these alterations suggests that such phenotypes are common at the locally advanced stages of the disease. Identification of gene dosage alterations and affected transcripts associated with the clinical outcome points to candidate biomarkers for chemoradioresistant disease and possible targets for therapeutic intervention.

Example 3. RYBP Protein Expression and Cellular Localization

Materials and Methods

Immunohistochemistry.

Pre-treatment tumor specimens were available in sufficient amounts for immunohistochemical study in 150 patients. Formalin-fixed, paraffin-embedded tissue sections from the patients and three cell lines (HeLa, SiHa, CaSki) were immunostained with RYBP (LifeSpan BioSciences, Seattle, Wash.) using the Dako EnVision™ FLEX+ detection system (Dako Corp., Denmark) manually. Heat induced epitope retrieval was performed with a PT Link using Envsion™ FLEX Target Retrieval Solution at high pH (Tris/EDTA buffer pH 9). Incubation time for the primary antibody was 45 minutes at room temperature. EnVision™ FLEX+ Rabbit LINKER was used for signal amplification of primary antibody and the reaction was visualized by EnVision™ FLEX DAB+ Chromogen. Placenta was used as positive control. As negative control, the primary antibody was substituted with normal rabbit IgG of the same concentration as the primary antibody.

The immunohistochemistry was evaluated by an experienced scientist at the Department of Pathology (R.H.) who was blinded for the clinical data. Both the staining intensity and percentage of positive tumor cells were given a score ranging from 0-3. For the percentage of positive tumor cells, the scores were as follows: 0, 0%; 1, 1-10%; 2, 11-50%; 3, >50%. The product (final score), ranging from 0-9 was used for further analysis. Normal cervix was given a score of 9, and a score less than that was considered reduced expression.

Cell Culture, siRNA Transfection, and Western Blotting.

The cervical cancer cell lines HeLa, SiHa and CaSki were grown in DMEM glutamax supplemented with 10% heat-inactivated fetal calf serum, penicillin, and streptomycin at 37° C. in a humidified atmosphere with 5% CO2. The cell lines were plated in 6-well plates 24 hours prior to transfection with siRNA. Each well received 20 µM RYBP siGENOME SMARTpool (Dharmacon, Chicago, Ill.) mixed with Oligofectamine Transfection Reagent (Invitrogen). Control cells were transfected with 20 µM siGENOME Non-Targeting siRNA Pool#1. The transfected cells were harvested after 96 hours. For Western blotting, transfected cells were lysed in lysis buffer (20 mM TrisHCl, pH 7.5, containing 137 mM NaCl, 10% glycerol, 1% Igepal) with protease inhibitors. Rabbit anti-RYBP polyclonal antibody was purchased from LifeSpan BioSciences and goat anti-rabbit IgGs were products of DAKO. Samples were separated on 8% Tris-HEPES-SDS polyacrylamide gels (Pierce Biotechnology, Rockford, Ill.), blotted on a PVDF membrane and visualized using LumiGLO Chemiluminescent substrate system (KPL, Gaithersburg, Md.).

Results

Figure 10:
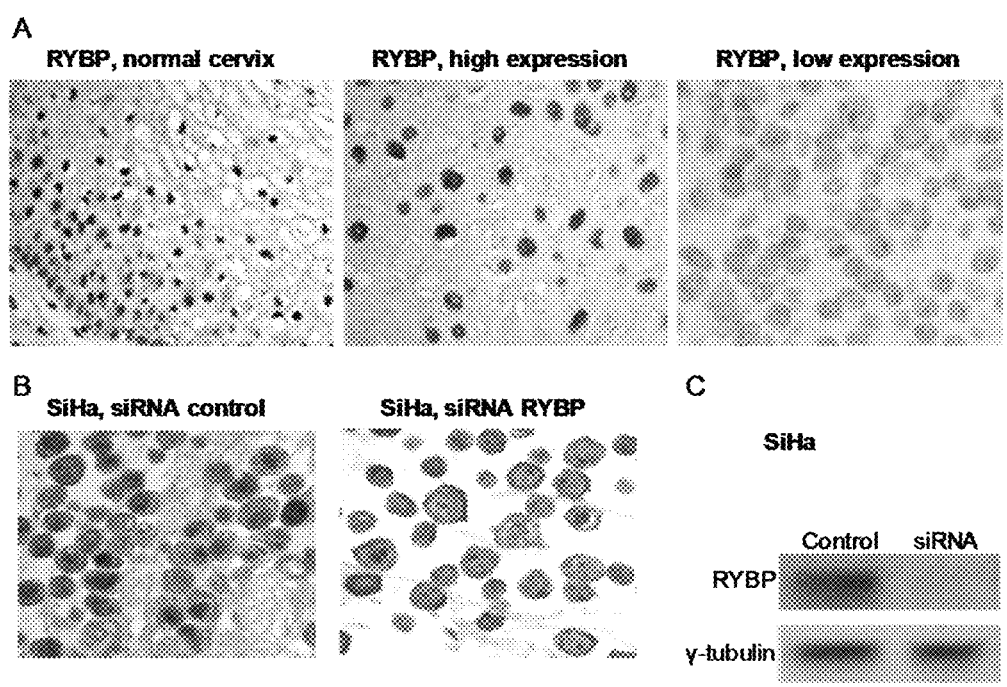
FIG. 10. (A) Immunohistochemical staining with RYBP antibody in normal cervix and cervical tumors with high and low nuclear expression of the protein. (B) Immunohistochemical staining with the RYBP antibody in SiHa cells transfected with negative siRNA control and siRNA RYBP. (C) Western blot of RYBP from SiHa cells transfected with negative siRNA control siRNA RYBP. Gamma-tubulin was used as a protein loading control. (D) Average RYBP immunohistochemical score of patients with no loss, moderate loss (−1<gene dosage<0) or severe loss (gene dosage≤−1) of 3p11.2-p14.2. Bars represent standard error. (E) Average RYBP gene expression of patients with low or high protein expression of RYBP. Bars represent standard error.
Figure 10:
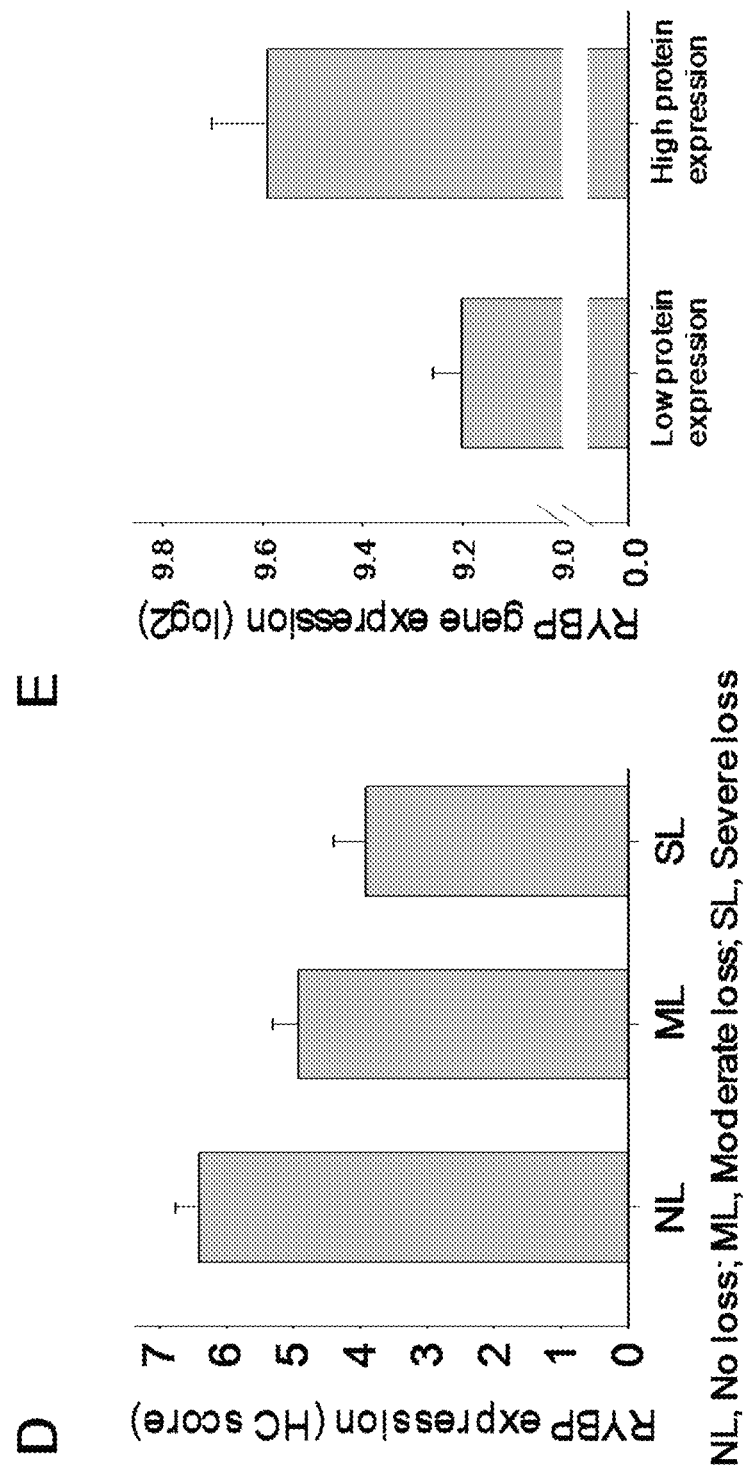

Since repression of the apoptosis pathway involving RYBP seemed to be characteristic of tumors with 3p loss, RYBP was studied further at the protein level with immunohistochemistry. Strong nuclear RYBP expression was seen in the epithelium of the normal cervix and in some of the cervical tumors, whereas other tumors showed minor nuclear expression (FIG. 10A). The cytoplasmic staining was weak and differed little within and among the tumors. To ensure that the nuclear expression was specific for RYBP, its expression in SiHa, HeLa, and CaSki cells before and after transfection with RYBP siRNA was compared. The transfection led to reduced nuclear staining compared to the negative siRNA control, whereas no change was seen in the cytoplasm (FIG. 10B and data not shown). Western blots confirmed that the RYBP expression was significantly reduced in the transfected cells (FIG. 10C and data not shown). We therefore concluded that RYBP was located in the nucleus and that the weak cytoplasmic staining in the cervical cancer samples probably reflected unspecific binding of the antibody applied.

Figure 11:
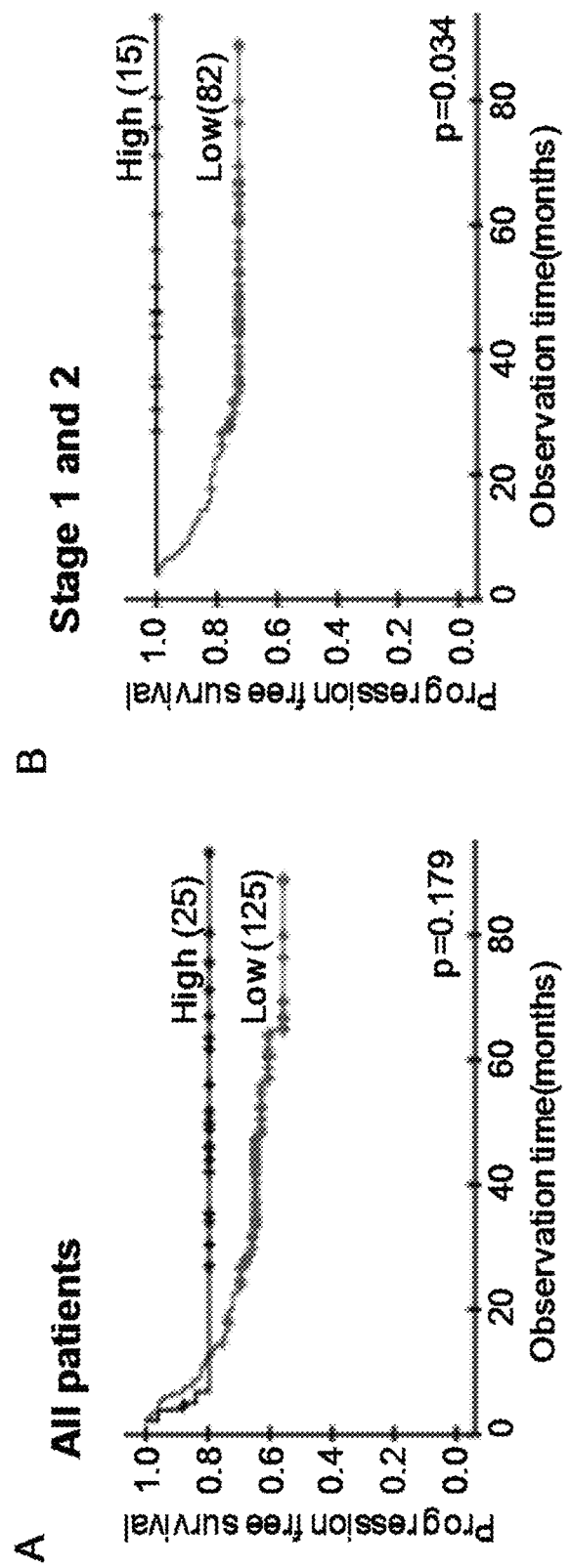
FIG. 11. Kaplan-Meier curves for progression free survival of cervical patients with high (black) and low (green) protein expression of RYBP. P-values in log rank test and number of patients are indicated. (A) All patients. (B) Patients with a stage 1 or 2 tumor.

Totally 125 tumors (83%) showed low nuclear RYBP expression compared to the normal cervix. The expression was significantly correlated both with gene dosage (p<0.001) and expression (p=<0.001) (FIG. 10D, E). Moreover, a clear tendency of reduced clinical outcome was seen for the patients with low RYBP expression compared to the others (FIG. 11A). The difference in outcome was significant when the patients with a stage 3 or 4a tumor were excluded (FIG. 11B). The predictive impact of RYBP protein expression for patients with stage 1 or 2 tumor was assessed by multivariate analysis together with tumor size and lymph node status, but did not show independent impact (data not shown).

Tables

TABLE 1

Patient and tumor characteristics.

| Characteristic | Basic cohort (n = 102) | Validation cohort (n = 41) |
|---|---|---|
| Histology (n) | | |
| Squamous | 96 | 40 |
| Adenocarcinoma | 1 | 0 |
| Adenosquamous carcinoma | 5 | 1 |
| HPV status (n)[a,b] | | |
| HPV16 | 65 | 35 |
| HPV18 | 7 | 0 |
| HPV16 + 18 | 11 | 1 |
| HPV other | 10 | 4 |
| HPV negative | 8 | 1 |
| FIGO stage (n) | | |
| 1B | 6 | 2 |
| 2 | 57 | 27 |
| 3 | 35 | 9 |
| 4A | 4 | 3 |
| Tumor size[c]: vol (cm$^3$)[d], diameter (cm)[e] | | |
| Median | 45.1, 4.4 | 36.6, 4.1 |
| Range | 2.8-321, 1.8-8.5 | 8.7-192, 2.5-7.2 |
| Pelvic lymph node status[c] (n) | | |
| Positive | 37 | 12 |
| Negative | 65 | 29 |
| Age (years) | | |
| Median | 56 | 55 |
| Range | 28-85 | 25-81 |
| Observation time (months) | | |
| Median | 42 | 31 |
| Range | 21-71 | 24-46 |
| Relapse | 32 | 12 |

[a]PCR on DNA was performed. The products were detected by polyacrylamide gel electrophoresis or the Agilent DNA 1000 kit (Agilent Technologies Inc., Germany).
[b]HPV status was not determined for one patient in the basic cohort due to lack of DNA for analysis.
[c]Tumor size and lymph node status were determined from pretreatment magnetic resonance (MR) images.
[d]Volume was calculated based on 3 orthogonal diameters (a, b, c) as (π/6) * abc.
[e]Diameter was calculated from tumor volume (4π/3) * r$^3$.

TABLE 2

Gene dosage alterations and correlating genes in locally advanced cervical cancer.

| Peak region[a] (Cytoband) | Peak region[a] (MB) | Freq.[b] (%) | Max./min. gene dosage[c] (copy no.) | Correlating genes[d] |
|---|---|---|---|---|
| Recurrent gain | | | | |
| 1p36.21-pter | 0-14.6 | 38 | 2 (4) | SLC35E2, UBE4B, AGTRAP |
| 1p32.1-p34.3 | 37.3-59.9 | 40 | 2 (4) | C1orf149, YRDC, RLF, EBNA1BP2, TACSTD2 |
| 1q21.1-q22 | 148.0-153.7 | 61 | 2.5 (6) | SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS |
| 3q26.1-qter[e] | 166.2-199.5 | 75 | 4.5 (9) | PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1 |
| 5p15.2-pter[e] | 1.0-12.1 | 47 | 4 (15) | CLPTM1L, MED10, FASTKD3, CCT5, DAP |
| 8q24.13-22 | 125.7-134.1 | 37 | 2 (4) | None |
| 8q24.3-qter | 144.5-146.3 | 38 | 2 (4) | TSTA3, FAM83H, CYC1 |
| 9p24.1-2[e] | 2.7-6.0 | 22 | 13.5 (27) | KIAA0020, RCL1 |
| 9q34.2-qter | 135.6-138.2 | 35 | 3.5 (7) | MRPS2 |
| 11q22.1-2[e] | 100.2-102.0 | 14 | 36 (72) | YAP1, BIRC3, BIRC2 |
| 19q13.11-qter | 40.3-63.8 | 36 | 10 (29) | SPINT2, PSMD8, CAPN12, MRPS12, RPS16, AP2S1, KDELR1, NUP62, ATF5, NKG7, ZNF787 |
| 20q11.21-22[e] | 30.0-33.0 | 45 | 3.4 (9) | POFUT1, KIF3B, MAPRE1, SNTA1, EIF2S2, AHCY |
| Xp11.22-pter[f] | 0-54.1 | 38 | 2.5 (5) | SLC25A6, CD99, ARSD, PNPLA4, PRPS2, PIR, CXorf15, PHKA2, PDHA1, RPS6KA3, PRDX4, |
| Xq28-qter | 148.5-154.9 | | 4 (8) | NSDHL, BCAP31, IDH3G, IRAK1, TAZ, LAGE3, UBL4A, FAM34, MTCP1 |
| Recurrent loss | | | | |
| 2q33.3-qter | 206.2-243.0 | 54 | 0.26 (1) | NDUFS1, SPAG16, MREG, SMARCAL1, AAMP, WNT10A, ZFAND2B, ANKZF1, STK11IP, FARSB, ACSL3, HRB, SP100, EIF4E2, COPS8, HDAC4, MTERFD2, PPP1R7 |
| 3p12.3-p14.2 | 60.9-81.6 | 61 | 0.26 (1) | RYBP, GBE1 |
| 4p13-p16.1 | 8.3-42.3 | 58 | 0.42 (1) | WDR1, UBE2K, PDS5A |
| 5q13.2[g] | 67.4-71.7 | 38 | 0 (0) | SMN2 |
| 5q14.2-q15 | 82.5-96.9 | 35 | 0.5 (1) | COX7C, TTC37, GLRX |
| 6q12-q23.2 | 67.0-132.9 | 42 | 0.43 (1) | LMBRD1, MYO6, HMGN3, SYNCRIP, MAP3K7, CCNC, C6orf203, FOXO3, AMD1, HDAC2, NT5DC1, DSE, |
| 7q34-qter | 139.3-158.8 | 35 | 0.43 (1) | PDIA4 |
| 8p12-pter | 0-31.9 | 32 | 0.34 (1) | XPO7, BIN3, BNIP3L, EPHX2, CCDC25, DCTN6, PPP2CB |
| 10q23.31[g] | 88.2-92.1 | 38 | 0 (0) | None |
| 11p14.3-pter | 0-24.4 | 40 | 0.5 (1) | COPB1, PSMA1, GTF2H1, TSG101 |
| 11p12 | 37.8-40.2 | 37 | 0.5 (1) | None |
| 11q22.3-qter | 105.1-134.5 | 63 | 0.35 (1) | PPP2R1B, C11orf57, TIMM8B, REXO2, C11orf60, TPAPPC4, H2AFX, POU2F3, ARHGEF12, SC5DL, ZNF202, CHEK1, APLP2, ZBTB44, SNX19 |
| 13q12.2-q21.32 | 27.5-67.4 | 46 | 0.33 (1) | ALG5, FAM48A, COG6, KIAA1704, GTF2F2, MED4, RNASEH2B |
| 17p11.2-pter | 0-19.1 | 38 | 0.27 (1) | SPAG7, MPDU1, LSMD1, CYB5D1, COPS23 |
| 21q21.1-3 | 18.3-28.6 | 35 | 0.28 (1) | ATP5J |
| Predictive loss | | | | |
| 3p11.2-p14.1 | 67.0-87.6 | 58 | 0.26 (1) | RYBP, GBE1 |

TABLE 2-continued

Gene dosage alterations and correlating genes in locally advanced cervical cancer.

| Peak region[a] (Cytoband) | Peak region[a] (MB) | Freq.[b] (%) | Max./min. gene dosage[c] (copy no.) | Correlating genes[d] |
|---|---|---|---|---|
| 13q13.1-q21.1 | 30.0-56.5 | 46 | 0.41 (1) | ALG5, FAM48A, COG6, KIAA1704, GTF2F2, MED4, RNASEH2B |
| 21q22.2-3 | 38.0-46.4 | 23 | 0.28 (1) | PCP4, RIPK4, PDXK |

[a]Peak region of the recurrent gains and losses is the minimum shared region surrounded by at least three patients. In cases of recurrent high level amplification or homozygote deletion, this event determines the peak region. Peak region of the predictive losses is the region selected by LASSO.
[b]Frequency is the median percentage of tumors with the alteration.
[c]Gene dosage is absolute DNA copy number divided by ploidy. Maximum (gain) or minimum (loss) gene dosage and corresponding copy number are listed.
[d]Genes within the peak region showing a correlation between gene dosage and expression are ordered by DNA location.
[e]Recurrent high level amplification detected within recurrent gain. Peak region is the region with more than 25% higher amplitude than surrounding region.
[f]Probably two different peak regions.
[g]Homozygote deletion within recurrent loss. Peak region is the region with a gene dosage of zero.

TABLE 3

Cox regression analysis of genetic losses and clinical variables.

| Covariate | Univariate analysis[a] | | | Multivariate analysis[a] | | |
|---|---|---|---|---|---|---|
| | P | HR | 95% CI | P | HR | 95% CI |
| Loss of 3p11.2-p14.1[b] | 0.003 | 0.27 | 0.11-0.66 | 0.018 | 0.33 | 0.13-0.83 |
| Loss of 13q13.1-q21.1[b] | 0.006 | 0.32 | 0.14-0.72 | 0.015 | 0.35 | 0.14-0.82 |
| Loss of 21q22.2-3[b] | 0.004 | 0.34 | 0.16-0.71 | 0.019 | 0.32 | 0.12-0.84 |
| Tumor size[c] | 0.001 | 4.5 | 1.9-10.5 | 0.001 | 5.5 | 1.9-15.5 |
| FIGO stage[d] | 0.004 | 2.9 | 1.4-5.9 | 0.072 | — | — |
| Total lymph node status[e] | 0.030 | 0.46 | 0.22-0.93 | 0.285 | — | — |

[a]P-value (P), hazard ratio (HR), and 95% confidence interval (CI) are listed.
[b]Semi-discrete gene dosage data of the most significant genomic clone within each region were used.
[c]Tumor size was divided in two groups based on the median size of 45.1 cm$^3$, corresponding to a median diameter of about 4.4 cm.
[d]FIGO stage was divided in two groups; 1b-2b and 3a-4a.
[e]Total includes pelvic and para aortal lymph nodes.

TABLE 4

Biological processes overrepresented among the correlating genes within recurrent and predictive regions.

| GO number | GO category | No. correlating genes | No. genes on the array | P-value | Correlating genes |
|---|---|---|---|---|---|
| Gains | | | | | |
| GO: 000815 | Biological process | 93[a] | 5824[a] | | |
| GO: 0006915 | Apoptosis | 13 (14.0%) | 434 (7.5%) | 0.026 | UBE4B, BIRC2, BIRC3, ATF5, BCAP31, CLPTM1L, |
| GO: 0005975 | Carbohydrate metabolism | 7 (7.5%) | 198 (3.4%) | 0.038 | PPP1R2, ARNT, PHKA2, POFUT1, PDHA1, TSTA3, |
| GO: 0006412 | Translation | 7 (7.5%) | 163 (2.8%) | 0.015 | EIF4G1, EIF4A2, EIF2S2, MRPS12, RPS16, EIF2S3, |
| GO: 0022613 | RNA-protein complex biogenesis | 7 (7.5%) | 89 (1.5%) | 0.001 | EIF4G1, EIF4A2, EIF2S2, EIF2S3, EBNA1BP2, NCBP2, |
| Losses | | | | | |
| GO: 000815 | Biological process | 62[a] | 5824[a] | | |
| GO: 0033036 | Macromolecule localization | 10 (16.1%) | 427 (7.3%) | 0.022 | BIN3, COPB1, COG6, XPO7, HRB, MYO6, PDIA4, SNX19, |
| GO: 0006091 | Generation of precursor metabolites and energy | 4 (6.5%) | 117 (2.0%) | 0.035 | ATP5J, COX7C, GBE1, NDUFS1 |

TABLE 4-continued

Biological processes overrepresented among the correlating genes within recurrent and predictive regions.

| GO number | GO category | No. correlating genes | No. genes on the array | P-value | Correlating genes |
|---|---|---|---|---|---|
| GO: 0006366 | Transcription from RNA polymerase II | 10 (16.1%) | 357 (6.1) | 0.004 | RYBP, FOXO3, GTF2F2, GTF2H1, MED4, MYO6, |
| GO: 0006325 | Establishment or maintenance of chromatin architecture | 5 (8.1%) | 140 (2.4%) | 0.016 | DSE, H2AFX, HDAC2, SMARCAL1, HDAC4 |

[a]Genes with GO annotation (biological process).

TABLE 5

Recurrent high-level amplifications and homozygous deletions in locally advanced cervical cancer.

| Peak region[a] (Cytoband) | Peak region[a] (MB) | Freq.[b] (%) | Max./min. gene dosage[c] (copy no.) | Correlating genes[d] |
|---|---|---|---|---|
| *Recurrent high level amplification* | | | | |
| 3q26.1-qter | 166.2-199.5 | 8 | 4.5 (9) | PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1 |
| 5p15.2-pter | 1.0-12.1 | 8 | 4 (15) | CLPTM1L, MED10, FASTKD3, CCT5, DAP |
| 9p24.1-2 | 2.7-6.0 | 4 | 13.5 (27) | KIAA0020, RCL1 |
| 11q13.2-3 | 68.6-70.6 | 4 | 10 (20) | FADD |
| 11q22.1-2 | 100.2-102.0 | 5 | 36 (72) | YAP1, BIRC3, BIRC2 |
| 20q11.21-22 | 30.0-33.0 | 5 | 3.4 (9) | POFUT1, KIF3B, MAPRE1, SNTA1, EIF2S2, AHCY |
| 21q22.11-2 | 32.9-39.6 | 4 | 7.5 (15) | TTC3, BRWD1 |
| *Homozygous deletion[e]* | | | | |
| 5q13.2 | 67.4-71.7 | 1 | 0 (0) | SMN2 |
| 6p21.1-p12.1 | 44.1-54.1 | 1 | 0 (0) | — |
| 8q24.23 | 136.6-139.3 | 1 | 0 (0) | — |
| 9p21.1-3 | 22.6-29.6 | 1 | 0 (0) | MOBKL2B |
| 10q23.31 | 88.2-92.1 | 3 | 0 (0) | — |
| 13q34 | 111.7-114.1 | 1 | 0 (0) | — |

[a]Peak region of high level amplifications is the region with more than 25% higher amplitude than surrounding region. Peak region of homozygote deletions is the region with a gene dosage of zero.
[b]Frequency is the median percentage of tumors with the alteration.
[c]Gene dosage is absolute DNA copy number divided by ploidy. Maximum (gain) or minimum (loss) gene dosage and the corresponding copy number are listed.
[d]Genes within the peak region showing a correlation between gene dosage and expression are ordered by DNA location.
[e]Homozygote deletions were seen in only few tumors and were not detected as recurrent in statistical analysis.

TABLE 6

Correlations between Illumina, cDNA, and gene dosage data for correlating genes[a].

| ReporterID | IlluminaID | Gene | cDNA vs gene dosage 95 patients | | cDNA vs gene dosage 52 patients | | cDNA vs Illumina 52 patients | | Illumina vs gene dosage | |
|---|---|---|---|---|---|---|---|---|---|---|
| | | | R | p | R | p | R | p | R | p |
| 129563 | ILMN_1762582 | ARNT | 0.407 | 0.000 | 0.403 | 0.004 | 0.412 | 0.003 | 0.411 | 0.003 |
| 814158 | ILMN_1669113 | ATF5 | 0.347 | 0.001 | 0.520 | 0.000 | 0.812 | 0.000 | 0.488 | 0.000 |
| 825312 | ILMN_1772929 | ATP5J | 0.369 | 0.002 | 0.421 | 0.007 | 0.611 | 0.000 | 0.368 | 0.010 |
| 877832 | ILMN_1853837 | BCAP31 | 0.327 | 0.001 | 0.225 | 0.111 | 0.866 | 0.000 | 0.280 | 0.047 |
| 782748 | ILMN_1708485 | BIN3 | 0.502 | 0.000 | 0.577 | 0.000 | 0.345 | 0.013 | 0.415 | 0.003 |
| 34852 | ILMN_1768194 | BIRC2 | 0.475 | 0.000 | 0.467 | 0.000 | 0.697 | 0.000 | 0.573 | 0.000 |
| 201890 | ILMN_2405684 | BIRC3 | 0.476 | 0.000 | 0.445 | 0.001 | 0.636 | 0.000 | 0.237 | 0.091 |
| 249618 | ILMN_1752802 | CLPTM1L | 0.367 | 0.001 | 0.484 | 0.002 | 0.517 | 0.000 | 0.701 | 0.000 |
| 343352 | ILMN_1779530 | COG6 | 0.403 | 0.000 | 0.510 | 0.000 | 0.622 | 0.000 | 0.451 | 0.002 |

TABLE 6-continued

Correlations between Illumina, cDNA, and gene dosage data for correlating genes[a].

| ReporterID | IlluminaID | Gene | cDNA vs gene dosage 95 patients | | cDNA vs gene dosage | | cDNA vs Illumina 52 patients | | Illumina vs gene dosage | |
|---|---|---|---|---|---|---|---|---|---|---|
| | | | R | p | R | p | R | p | R | p |
| 897971 | ILMN_1699112 | COPB1 | 0.345 | 0.001 | 0.579 | 0.000 | 0.468 | 0.000 | 0.556 | 0.000 |
| 884480 | ILMN_1798189 | COX7C | 0.500 | 0.000 | 0.341 | 0.017 | 0.609 | 0.000 | 0.407 | 0.004 |
| 814381 | ILMN_2112493 | DAP | 0.404 | 0.000 | 0.565 | 0.000 | 0.790 | 0.000 | 0.621 | 0.000 |
| 487082 | ILMN_1706498 | DSE | 0.378 | 0.000 | 0.365 | 0.010 | 0.586 | 0.000 | 0.444 | 0.002 |
| 22918 | ILMN_1768127 | EBNA1BP2 | 0.293 | 0.004 | 0.242 | 0.086 | 0.696 | 0.000 | 0.352 | 0.012 |
| 469151 | ILMN_1798014 | EIF2S2 | 0.508 | 0.000 | 0.571 | 0.000 | 0.444 | 0.001 | 0.439 | 0.001 |
| 810237 | ILMN_1665717 | EIF2S3 | 0.427 | 0.000 | 0.248 | 0.076 | 0.492 | 0.000 | 0.320 | 0.021 |
| 307532 | ILMN_1685722 | EIF4A2 | 0.434 | 0.000 | 0.459 | 0.000 | 0.633 | 0.000 | 0.552 | 0.000 |
| 25988 | ILMN_2370772 | EIF4G1 | 0.468 | 0.000 | 0.314 | 0.038 | 0.636 | 0.000 | 0.446 | 0.002 |
| 809453 | ILMN_1802376 | FAM48A | 0.415 | 0.000 | 0.349 | 0.016 | 0.492 | 0.000 | 0.344 | 0.018 |
| 133158 | ILMN_1750160 | FASTKD3 | 0.619 | 0.000 | 0.782 | 0.000 | 0.645 | 0.000 | 0.608 | 0.000 |
| 82171 | ILMN_1687940 | FOXO3 | 0.335 | 0.002 | 0.315 | 0.033 | 0.618 | 0.000 | 0.359 | 0.015 |
| 289551 | ILMN_2389273 | FXR1 | 0.435 | 0.000 | 0.530 | 0.000 | 0.752 | 0.000 | 0.554 | 0.000 |
| 127509 | ILMN_1789702 | GBE1 | 0.347 | 0.001 | 0.271 | 0.057 | 0.465 | 0.000 | 0.365 | 0.009 |
| 754085 | ILMN_1745798 | GTF2F2 | 0.344 | 0.001 | 0.473 | 0.000 | 0.700 | 0.000 | 0.480 | 0.000 |
| 811942 | ILMN_2157957 | GTF2H1 | 0.341 | 0.001 | 0.323 | 0.021 | 0.449 | 0.000 | 0.215 | 0.130 |
| 256664 | ILMN_2200331 | H2AFX | 0.388 | 0.000 | 0.305 | 0.036 | 0.495 | 0.000 | 0.332 | 0.021 |
| 502669 | ILMN_1767747 | HDAC2 | 0.439 | 0.000 | 0.471 | 0.000 | 0.521 | 0.000 | 0.652 | 0.000 |
| 1606829 | ILMN_1764396 | HDAC4 | 0.357 | 0.001 | 0.397 | 0.005 | 0.395 | 0.004 | 0.301 | 0.036 |
| 843319 | ILMN_1792497 | HRB | 0.425 | 0.000 | 0.466 | 0.000 | 0.292 | 0.036 | 0.415 | 0.002 |
| 810942 | ILMN_1802706 | IDH3G | 0.428 | 0.000 | 0.486 | 0.000 | 0.789 | 0.000 | 0.275 | 0.051 |
| 795282 | ILMN_1664641 | MED4 | 0.568 | 0.000 | 0.502 | 0.000 | 0.445 | 0.001 | 0.446 | 0.003 |
| 131653 | ILMN_2371964 | MRPS12 | 0.455 | 0.000 | 0.521 | 0.000 | 0.785 | 0.000 | 0.548 | 0.000 |
| 810979 | ILMN_1815043 | MRPS2 | 0.365 | 0.001 | 0.333 | 0.018 | 0.495 | 0.000 | 0.507 | 0.000 |
| 470216 | ILMN_1727080 | MYO6 | 0.373 | 0.000 | 0.219 | 0.122 | 0.298 | 0.032 | 0.373 | 0.007 |
| 26711 | ILMN_1720442 | NCBP2 | 0.494 | 0.000 | 0.442 | 0.002 | 0.590 | 0.000 | 0.682 | 0.000 |
| 753457 | ILMN_1728810 | NDUFS1 | 0.431 | 0.000 | 0.405 | 0.004 | 0.383 | 0.005 | 0.476 | 0.000 |
| 795439 | ILMN_2323491 | NUP62 | 0.318 | 0.002 | 0.438 | 0.002 | 0.281 | 0.044 | 0.451 | 0.001 |
| 134439 | ILMN_1712687 | PAK2 | 0.304 | 0.003 | 0.245 | 0.093 | 0.414 | 0.002 | 0.568 | 0.000 |
| 137836 | ILMN_2269002 | PDCD10 | 0.588 | 0.000 | 0.646 | 0.000 | 0.775 | 0.000 | 0.705 | 0.000 |
| 80374 | ILMN_1772369 | PDHA1 | 0.327 | 0.001 | 0.177 | 0.214 | 0.743 | 0.000 | 0.207 | 0.144 |
| 248454 | ILMN_1815261 | PDIA4 | 0.357 | 0.001 | 0.289 | 0.049 | 0.621 | 0.000 | 0.445 | 0.002 |
| 454475 | ILMN_1814074 | PHKA2 | 0.470 | 0.000 | 0.298 | 0.036 | 0.656 | 0.000 | 0.418 | 0.003 |
| 112131 | ILMN_1776076 | POFUT1 | 0.303 | 0.003 | 0.476 | 0.000 | 0.662 | 0.000 | 0.457 | 0.000 |
| 2191807 | ILMN_1773613 | POU2F3 | 0.399 | 0.000 | 0.257 | 0.113 | 0.295 | 0.052 | 0.120 | 0.431 |
| 769657 | ILMN_1683044 | PPP1R2 | 0.524 | 0.000 | 0.551 | 0.000 | 0.558 | 0.000 | 0.637 | 0.000 |
| 125148 | ILMN_1813766 | RCL1 | 0.603 | 0.000 | 0.492 | 0.000 | 0.719 | 0.000 | 0.515 | 0.000 |
| 686733 | ILMN_1782488 | RNASEH2B | 0.379 | 0.000 | 0.457 | 0.002 | 0.524 | 0.000 | 0.267 | 0.079 |
| 853151 | ILMN_1651850 | RPS16 | 0.440 | 0.000 | 0.418 | 0.002 | 0.042 | 0.766 | 0.169 | 0.236 |
| 795453 | ILMN_1721842 | RYBP | 0.494 | 0.000 | 0.606 | 0.000 | 0.522 | 0.000 | 0.480 | 0.000 |
| 450131 | ILMN_1752111 | SMARCAL1 | 0.437 | 0.000 | 0.614 | 0.000 | 0.521 | 0.000 | 0.625 | 0.000 |
| 295255 | ILMN_1788211 | SNX19 | 0.422 | 0.000 | 0.417 | 0.006 | 0.671 | 0.000 | 0.440 | 0.003 |
| 884657 | ILMN_1738938 | TIMM8B | 0.432 | 0.000 | 0.649 | 0.000 | 0.717 | 0.000 | 0.587 | 0.000 |
| 878744 | ILMN_1747146 | TSG101 | 0.538 | 0.000 | 0.554 | 0.000 | 0.632 | 0.000 | 0.549 | 0.000 |
| 739126 | ILMN_1697777 | TSTA3 | 0.387 | 0.000 | 0.336 | 0.020 | 0.336 | 0.000 | 0.222 | 0.128 |
| 346292 | ILMN_1675674 | UBE4B | 0.304 | 0.003 | 0.460 | 0.001 | 0.661 | 0.000 | 0.367 | 0.011 |
| 206545 | ILMN_2174884 | XPO7 | 0.400 | 0.000 | 0.434 | 0.001 | 0.742 | 0.000 | 0.614 | 0.000 |
| 126702 | ILMN_1792990 | ZNF202 | 0.333 | 0.001 | 0.355 | 0.013 | 0.289 | 0.038 | 0.387 | 0.006 |

[a]Data for genes in FIG. 5 are shown. The results are typical for all correlating genes.

REFERENCES

Lyng et al., Genome Biology 2008, 9:R86
Bovelstad H M et al. Bioinformatics 2007, 23: 2080-2087.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of this invention are intended to be within the scope of the following claims.

The invention claimed is:

1. A method for detectably labelling a set of gene products from a human cervical cancer sample comprising:
   isolating RNA from a human cervical cancer sample from a patient with locally advanced cervical cancer and reverse transcribing said isolated RNA to provide complementary DNA corresponding to at least three gene products selected from the group consisting of RYBP, GBE1, ALG5, FAM48A, COG6, KIAA1704, GTF2F2, MED4, RNASEH2B and PRDM15 gene products
   amplifying said complementary DNA by polymerase chain reaction with primers specific for complementary DNA corresponding to at least three gene products selected from the group consisting of RYBP, GBE1, ALG5, FAM48A, COG6, KIAA1704, GTF2F2, MED4, RNASEH2B and PRDM15 gene products in the presence of a probe to provide detectably labeled amplified complementary DNA;

quantitating the expression of said at least three gene products selected from the group consisting of RYBP, GBE1, ALG5, FAM48A, COG6, KIAA1704, GTF2F2, MED4, RNASEH2B and PRDM15 gene products; and providing a prognosis based on the expression of said at least three gene products selected from the group consisting of RYBP, GBE1, ALG5, FAM48A, COG6, KIAA1704, GTF2F2, MED4, RNASEH2B and PRDM15 gene products.

2. The method of claim 1 further comprising:

determining the expression levels of at least one additional gene selected from the group consisting of SLC35E2, UBE4B, AGTRAP, C1orf149, YRDC, RLF, EBNA1BP2, TACSTD2, SF3B4, ENSA, GOLPH3L, ARNT, LASS2, ANXA9, POGZ, CGN, SNX27, C1orf77, ILF2, DENN4B, SLC39A1, UBE2Q1, EFNA1, KRTCAP2, MUC1, FDPS, PDCD10, PHC3, ZNF639, FXR1, PARL, DVL3, ABCF3, ALG3, EIF4G1, SFRS10, DGKG, EIF4A2, RFC4, CCDC50, PPP1R2, PAK2, NCBP2, DLG1, BDH1, FLYTTD1, CLPTM1L, MED10, FASTKD3, CCT5, DAP, TSTA3, FAM83H, CYC1, KIAA0020, RCL1, MRPS2, YAP1, BIRC3, BIRC2, SPINT2, PSMD8, CAPN12, MRPS12, RPS16, AP2S1, KDELR1, NUP62, ATF5, NKG7, ZNF787, POFUT1, KIF3B, MAPRE1, SNTA1, EIF2S2, AHCY, SLC25A6, CD99, ARSD, PNPLA4, PRPS2, PIR, CXorf15, PHKA2, PDHA1, RPS6KA3, PRDX4, EIF2S3, USP9X, DDX3X, NDUFB11, UBA1, EBP, PLP2, JARID1C, SMC1A, HUWE1, NSDHL, BCAP31, IDH3G, IRAK1, TAZ, LAGE3, UBL4A, FAM34, MTCP1, NDUFS1, SPAG16, MREG, SMARCAL1, AAMP, WNT10A, ZFAND2B, ANKZF1, STK1HP, FARSB, ACSL3, HRB, SP100, EIF4E2, COPSE, HDAC4, MTERFD2, PPP1R7, WDR1, UBE2K, PDS5A, SMN2, COX7C, TTC37, GLRX, LMBRD1, MYO6, HMGN3, SYNCRIP, MAP3K7, CCNC, C6orf203, FOXO3, AMD1, HDAC2, NT5DC1, DSE, NUS1, ECHDC1, PDIA4, XPO7, BIN3, BNIP3L, EPHX2, CCDC25, DCTN6, PPP2CB, COPB1, PSMA1, GTF2H1, TSG101, PPP2R1B, C11orf57, TIMM8B, REXO2, C11orf60, TRAPPC4, H2AFX, POU2F3, ARHGEF12, SC5DL, ZNF202, CHEK1, APLP2, ZBTB44, SNX19, SPAG7, MPDU1, LSMD1, CYB5D1, COPS23, and ATP5J.

3. The method of claim 1, wherein said three or more genes are MED4, GBE1, and RYBP.

4. The method of claim 1, wherein said three or more genes are MED4, GBE1, FAM48A, and RYBP.

5. The method of claim 1, wherein said three or more genes are MED4, GBE1, FAM48A, GTF2F2, and RYBP.

6. The method of claim 1, wherein said three or more genes are MED4, GBE1, FAM48A, GTF2F2, COG6, and RYBP.

7. The method of claim 1, wherein said three or more genes are MED4, GBE1, FAM48A, GTF2F2, COG6, RIPK4, and RYBP.

8. The method of claim 1, wherein said three or more genes are MED4, GBE1, FAM48A, GTF2F2, COG6, RIPK4, KIAA1704, and RYBP.

9. The method of claim 1, wherein said three or more genes are MED4, GBE1, FAM48A, GTF2F2, COG6, RIPK4, KIAA1704, ALG5, and RYBP.

* * * * *

UNITED STATES PATENT AND TRADEMARK OFFICE
CERTIFICATE OF CORRECTION

PATENT NO. : 9,809,859 B2  
APPLICATION NO. : 14/664346  
DATED : November 7, 2017  
INVENTOR(S) : Heidi Lyng et al.

It is certified that error appears in the above-identified patent and that said Letters Patent is hereby corrected as shown below:

In the Claims

Column 56, Claim 2, Line 2 should read:  
"ANKZF1, STK11IP, FARSB, ACSL3, HRB, SP100,"

Column 56, Claim 2, Line 3 should read:  
"EIF4E2, COPS8, HDAC4, MTERFD2, PPP1R7,"

Signed and Sealed this  
Twenty-sixth Day of December, 2017

Joseph Matal  
*Performing the Functions and Duties of the*  
*Under Secretary of Commerce for Intellectual Property and*  
*Director of the United States Patent and Trademark Office*